US007601519B2

(12) United States Patent
Matsui et al.

(10) Patent No.: US 7,601,519 B2
(45) Date of Patent: *Oct. 13, 2009

(54) METHOD FOR PRODUCING PURINE NUCLEOSIDE BY FERMENTATION

(75) Inventors: Hiroshi Matsui, Kawasaki (JP); Hisashi Kawasaki, Kawasaki (JP); Megumi Shimaoka, Kawasaki (JP); Yasuhiro Takenaka, Kawasaki (JP); Osamu Kurahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1 day.

This patent is subject to a terminal disclaimer.

(21) Appl. No.: 11/682,114

(22) Filed: Mar. 5, 2007

(65) Prior Publication Data

US 2007/0166799 A1 Jul. 19, 2007

Related U.S. Application Data

(62) Division of application No. 09/462,472, filed as application No. PCT/JP98/03239 on Jul. 17, 1998.

(30) Foreign Application Priority Data

Jul. 18, 1997 (JP) .................................. 9-194603

(51) Int. Cl.
*C12P 19/26* (2006.01)
*C12P 19/28* (2006.01)
*C12P 19/38* (2006.01)
*C12N 9/00* (2006.01)
*C12N 9/10* (2006.01)
*C12N 1/20* (2006.01)
*C07H 21/04* (2006.01)

(52) U.S. Cl. ............................ 435/87; 435/84; 435/85; 435/183; 435/193; 435/252.32; 536/23.2

(58) Field of Classification Search .................. 435/84, 435/85, 87, 183, 193, 252.32; 536/23.2
See application file for complete search history.

(56) References Cited

U.S. PATENT DOCUMENTS

| 3,152,966 | A | 10/1964 | Kinoshita et al. |
| 3,258,408 | A | 6/1966 | Okumura et al. |
| 3,298,923 | A | 1/1967 | Banno et al. |
| 3,736,228 | A | 5/1973 | Nakayama et al. |
| 5,766,925 | A | 6/1998 | Sugimoto et al. |
| 5,804,414 | A | 9/1998 | Moriya et al. |
| 5,876,983 | A | 3/1999 | Sugimoto et al. |
| 5,919,694 | A | 7/1999 | Sugimoto et al. |
| 2004/0086985 | A1 | 5/2004 | Matsui et al. |

FOREIGN PATENT DOCUMENTS

| EP | 0 282 989 | 9/1988 |
| EP | 0 406 436 | 1/1991 |
| EP | 1 004 663 | 5/2000 |
| EP | 1 217 076 | 6/2002 |
| JP | 63-248394 | 10/1888 |

OTHER PUBLICATIONS

Raushel et al. Biochemistry. Jun. 22, 1999;38(25):7891-9.*
Zhou et al. J Biol Chem. Mar. 4, 1994;269(9):6784-9.*
Mushegian et al. Protein Sci. Jul. 1994;3(7):1081-8.*
Egan et al. J Bacteriol. Jul. 1992;174(14):4638-46.*
Westh Hansen et al. Eur J Biochem. Oct. 15, 1987;168(2):385-91.*
Neuhard et al. "Purines and Pyrimidines." In: *Escherichia coli* and *Salmonella typhimurium*: Cellular and Molecular Biology. Edited by F. C. Neidhardt. Washington, D.C: American Society for Microbiology, 1987, vol. 1, pp. 445-473.*
U.S. Appl. No. 11/682,103, filed Mar. 5, 2007, Matsui et al.
U.S. Appl. No. 11/682,083, filed Mar. 5, 2007, Matsui et al.
U.S. Appl. No. 11/682,155, filed Mar. 5, 2007, Matsui et al.
Arcady R. Mushegian, et al., "Unexpected Sequence Similarity Between Nucleosidases and Phosphoribosyltransferases of Different Specificity", Protein Science, 1994, 1081-1088.
Zengyi Chang, et al., "Deduced Amino Acid Sequence of *Escherichia coli* Adenosine Deaminase Reveals Evolutionarily Conserved Amino Acid Residues: Implications for Catalytic Function", Biochemistry, vol. 30, No. 8, 1991, pp. 2273-2280.
Anna Modrak-Wojcik, et al., "Molecular Architecture of *E. coli* Purine Nucleoside Phosphorylase Studied by Analytical Ultracentrifugation and CD Spectroscopy", Protein Science, vol. 15, No. 7, 2006, pp. 1794-1800.
Wolfe, et al., Accession J04199, published Apr. 26, 1993.
Fraenkel, D., et al., "Glucose and Gluconate Metabolism in an *Escherichia coli* Mutant Lacking Phosphoglucose Isomerase," Journal of Bacteriology, vol. 93, No. 5, May 1967, pp. 1571-1578.
Levine, R. A., et al., Mol Gen Genet, vol. 181, pp. 313-318, "Selection for Purine Regulatory Mutants in an *E. coli* Hypoxanthine Phosphoribosyl Transferase-Guanine Phosphoribosyl Transferase Double Mutant," 1981.

(Continued)

*Primary Examiner*—Christian L Fronda
(74) *Attorney, Agent, or Firm*—Oblon, Spivak, McClelland, Maier & Neustadt, L.L.P.

(57) ABSTRACT

A microorganism which has a gene encoding an enzyme in which feedback inhibition is desensitized by substitution of one or two amino acids in PRPP amidotransferase encoded by purF of *Escherichia coli*, a gene encoding a protein which is an inactivated repressor of purine nucleotide biosynthesis encoded by purR, a gene encoding an enzyme which is inactivated purine nucleoside phosphorylase encoded by deoD, a gene encoding an enzyme which is inactivated succinyl-AMP synthase encoded by purA, a gene encoding an enzyme which is inactivated 6-phosphogluconate dehydrase encoded by edd, a gene encoding an enzyme which is inactivated phosphoglucose isomerase encoded by pgi and like is bred and a purine nucleoside is produced by culturing the microorganism.

9 Claims, 3 Drawing Sheets

OTHER PUBLICATIONS

Bower, S. B., et al., The Journal of Biological Chemistry, vol. 264, No. 17, pp. 10287-10297, "Characterization of the *Escherichia coli* PRS A1-Encoded Mutant Phosphoribsylpyrophosphate Synthetase Identifies a Divalent Cation-Nucleotide Binding Site", Jun. 15, 1989.

Zhou, G., et al., The Journal of Biological Chemistry, vol. 269, No. 9, pp. 6787-6789, "Binding of Purine Nucleotides to Two Regulatory Sites Results in Synergistic Feedback Inhibition of Glutamine 5-Phosphorbosylpyrophosphate Amidotransferase," Mar. 4, 1994.

Neuhard, et al., "Purines and Pyrimidines." In: *Escherichia coli* and *Salmonella typhimurium*: Cellular and Molecular Biology. Edited by F. C. Neidhardt. Washington, DC: American Society for Microgiology, 1987, vol. 1, pp. 445-473.

Mascarenhas, et al., Appl Environ Microbiol. Oct. 1991; 57(10):2995-2999.

Gelpi. J Chromatogr A. May 26, 1995; 703(1-2):59-80.

Rolfes, et al., J Biol Chem. Dec. 25, 1988; 263(36):19653-19661.

Accession P09452 Mar. 1, 1989.

Blattner, F. R., et al., "The Comple Genome Sequence of *Escherichia coli* K-12," Science, vol. 277, Sep. 5, 1997, pp. 1453-1462.

Japanese Patent Official Gazette No. 3117707 (Corresponds to JP 2-500062).

Wolfe, S. A., et al., "Nucleotide Sequence and Analysis of the purA Gene Encoding Adenylosuccinate Synthetase of *Escherichia coli* K12," Journal of Biological Chemistry, vol. 263, No. 35, Dec. 15, 1988, pp. 19147-19153.

Choi, K. Y., et al., "Mutagenesis of Amino Acid Residues Required for Binding of Corepressors to the Purine Repressor," Journal of Biological Chemistry, vol. 269, No. 39, Sep. 30, 1994, pp. 24066-24072.

Mori, H., at al., "Cloning of a Guanosine-Inosine Kinase Gene of *Escherichia coli* and Characterization of the Purified Gene Product," Journal of Bacteriology, vol. 177, No. 17, Sep. 1995, pp. 4921-4926.

Andrews, S. C., et al., "Nucleotide Sequence of the Gene Encoding the GMP Reductase of *Escherichia coli* K12," Biochem. J., vol. 255, No. 1, Oct. 1, 1988, pp. 35-43.

Egan, S. E., et al., "Molecular Characterization of the Entner-Doudoroff Pathway in *Escherichia coli*: Sequence Analysis and Localization of Promoters for the edd-eda Operon," Journal of Bacteriology, vol. 174, No. 14, Jul. 1992, pp. 4638-4646.

Seeger, C., et al., "Identification and Characterization of the Genes (xapA, xapB, and xapR) Involved in Xanthosine Catabolism in *Escherichia coli*," Journal of Bacteriology, vol. 177, No. 19, Oct. 1995, pp. 5506-5516.

Selkagaku Jiten (Dictionary of Biochemistry) 2nd edition, Tokyo Kagaku Doujin (1990), pp. 1147-1151.

Bower, S. B., et al., The Journal of Biological Chemistry, vol. 264, No. 17, pp. 10287-10291, "Characterization of the *Escherichia coli* PRS A1-Encoded Mutant Phosphoribsylpyrophosphate Synthetase Identifies a Divalent Cation-Nucleotide Binding Site", Jun. 15, 1989.

Zhou, G., et al., The Journal of Biological Chemistry, vol. 269, No. 9, pp. 6784-6789, "Binding of Purine Nucleotides to Two Regulatory Sites Results in Synergistic Feedback Inhibition of Glutamine 5-Phosphorbosylpyrophosphate Amidotransferase," Mar. 4, 1994.

* cited by examiner

METHOD FOR PRODUCING PURINE NUCLEOSIDE BY FERMENTATION

CROSS-REFERENCE TO RELATED APPLICATIONS

The present application is a divisional of U.S. Ser. No. 09/462,472, filed on Jan. 14, 2000, which is a National Stage (371) of PCT/JP98/03239 filed on Jul. 17, 1998, which claims priority to JP 09-194603, filed on Jul. 18, 1997.

TECHNICAL FIELD

The present invention relates to a method for producing purine nucleosides such as inosine and guanosine which are important as raw materials for syntheses of 5'-inosinic acid and 5'-guanylic acid, respectively, and a novel microorganism used for the production.

BACKGROUND ART

For the production of inosine and guanosine by fermentation, there have been known methods utilizing adenine auxotrophic strains or such strains further imparted with drug resistance against various drugs such as purine analogues, which strains belong to the genus *Bacillus* (Japanese Patent Publication Nos. 38-23039 (1963), 54-17033 (1979), 55-2956 (1980), and 55-45199 (1980), Japanese Patent Application Laid-Open No. 56-162998 (1981), Japanese Patent Publication Nos. 57-14160 (1982) and 57-41915 (1982), and Japanese Patent Application Laid-Open No. 59-42895 (1984)), or the genus *Brevibacterium* (Japanese Patent Publication Nos. 51-5075 (1976) and 58-17592 (1972), and Agric. Biol. Chem., 42, 399 (1978)) and the like.

Conventional acquisition of such mutant strains comprises subjecting microorganisms to a mutagenesis treatment such as UV irradiation and nitrosoguanidine (N-methyl-N'-nitro-N-nitrosoguanidine) treatment and selecting a desired strain by using a suitable selection medium. On the other hand, breeding of such mutant strains by the use of genetic engineering techniques have also been practiced for strains belonging to the genus *Bacillus* (Japanese Patent Application Laid-Open Nos. 58-158197 (1983), 58-175493 (1983), 59-28470 (1984), 60-156388 (1985), 1-27477 (1989), 1-174385 (1989), 3-58787 (1991), 3-164185 (1991), 5-84067 (1993), and 5-192164 (1993)) and the genus *Brevibacterium* (Japanese Patent Application Laid-Open No. 63-248394 (1988)).

DISCLOSURE OF INVENTION

The object of the present invention is to create a microorganism suitable for the production of the purine nucleoside by fermentation.

To achieve the aforementioned object, the present inventors conceived an idea of imparting purine nucleoside-producing ability to a bacterial strain of the genus *Escherichia*, which is different in the genus from microorganisms which have hitherto been used for the production of the purine nucleoside by fermentation, and successfully realized it. Thus, the present invention has been completed.

Thus, the present invention provides a microorganism belonging to the genus *Escherichia* and having purine nucleoside-producing ability.

Specifically, the present invention provides the microorganism which has acquired the purine nucleoside-producing ability because of an increase of an activity of an enzyme involved in the purine nucleoside biosynthesis in cells of the microorganism. More specifically, the present invention provides the microorganism which has acquired the purine nucleoside-producing ability because of an increase of an expression amount of a gene for an enzyme involved in the purine nucleoside biosynthesis, and the microorganism which has acquired the purine nucleoside-producing ability because of deregulation of control of an enzyme involved in the purine nucleoside biosynthesis.

The enzyme involved in the purine nucleoside biosynthesis may be, for example, phosphoribosyl pyrophosphate (PRPP) amidotransferase and phosphoribosyl pyrophosphate (PRPP) synthetase.

As a means of desensitizing the control of an enzyme involved in purine nucleoside biosynthesis, for example, deficiency of a purine repressor can be mentioned.

The present invention further provides the microorganism which has acquired the purine nucleoside-producing ability because of blockage of a reaction branching from the purine nucleoside biosynthesis and leading to another metabolite.

Examples of the reaction branching from the purine nucleoside biosynthesis and leading to another metabolite include, for example, those catalyzed by an enzyme selected from succinyl-adenosine monophosphate (AMP) synthase, purine nucleoside phosphorylase, adenosine deaminase, inosine-guanosine kinase, guanosine monophosphate (GMP) reductase, 5-phosphogluconate dehydrase, phosphoglucose isomerase, adenine deaminase, and xanthosine phosphorylase.

The present invention further provides the microorganism which is enhanced in the purine nucleoside-producing ability because of weakening of incorporation of a purine nucleoside into cells of the microorganism.

The incorporation of the purine nucleoside into cells of the microorganism may be weakened by blockage of a reaction involved in the incorporation of the purine nucleoside into cells of the microorganism. An example of the reaction involved in the incorporation of the purine nucleoside into cells of the microorganism is a reaction catalyzed by nucleoside permease.

The present invention further provides a method for producing a purine nucleoside by fermentation comprising culturing the aforementioned microorganism in a culture medium to produce and accumulate the purine nucleoside in the medium, and collecting the purine nucleoside.

The present invention described in details below.

(1) Microorganism Belonging to the Genus *Escherichia* and Having Purine Nucleoside-Producing Ability As examples of the microorganism belonging to the genus *Escherichia* used in the present invention, *Escherichia coli* (*E. coli*) and the like can be mentioned. When *E. coli* strains are bred by genetic engineering techniques, *E. coli* K12 strain may be utilized.

The term "purine nucleoside" herein used include, for example, inosine, guanosine, and adenosine.

The term "purine nucleoside-producing ability" herein used means ability to produce and accumulate a purine nucleoside in a medium. The term "having purine nucleoside-producing ability" means that the microorganism belonging to the genus *Escherichia* produces and accumulates a purine nucleoside in a medium in a larger amount than a wild strain of *E. coli* such as W3110 strain, preferably means that the microorganism produces and accumulates inosine in a medium in an amount of not less than 50 mg/L, more preferably not less than 100 mg/L, still more preferably not less than 200 mg/L, most preferably not less than 500 mg/L under the condition described in Example 1 below.

In order to breed a microorganism belonging to the genus *Escherichia* and having purine nucleoside-producing ability, it may be adopted breeding by increasing an activity of an enzyme involved in the purine nucleoside biosynthesis in cells of the microorganism, for example, breeding by increasing an expression amount of a gene for the enzyme involved in the purine nucleoside biosynthesis. Alternatively, breeding by desensitizing control of an enzyme involved in the purine nucleoside biosynthesis may be adopted.

Furthermore, breeding by blocking a reaction branching from purine nucleoside biosynthesis and leading to another metabolite and breeding by weakening of incorporation of a purine nucleoside into cells of the microorganism.

(2) Microorganism in which an Activity of an Enzyme Involved in Purine Nucleoside Biosynthesis in Cells of the Microorganism is Increased All the enzymes involved in the purine nucleoside biosynthesis and all the reactions catalyzed by those enzymes in microorganisms belonging to the genus *Escherichia* have already been elucidated (*Escherichia coli* and *Salmonella*, CELLULAR AND MOLECULAR BIOLOGY, Second Edition vol. 1 and vol. 2, ASM PRESS, WASHINGTON D.C.). The purine nucleoside-producing ability can be imparted by increasing an activity of an enzyme catalyzing a rate-limiting reaction among the enzymes. An example of the enzyme catalyzing a reaction of rate-limiting step is PRPP amidotransferase or PRPP synthetase.

Examples of means of increasing an activity of an enzyme involved in the purine nucleoside biosynthesis in cells are explained below but are not limited thereto.

As a means of increasing the activity of the enzyme involved in the purine nucleoside biosynthesis in cells, increasing an expression amount of the gene for the enzyme may be mentioned.

Examples of means of increasing the expression amount of the gene include improvement of a regulatory region of the gene and increase of a copy number of the gene, but are not limited thereto.

The improvement of the regulatory region means making modification thereto to increase a transcription amount of a gene. For example, a promoter can be enhanced by, for example, introducing a mutation into the promoter to increase a transcription amount of a gene located downstream of the promoter. Besides introducing a mutation into a promoter, another promoter which functions in microorganisms such as lac, trp, tac, trc, and PL may be newly introduced. Further, an enhancer may be newly introduced to increase the transcription amount of the gene. Introduction of a gene such as a promoter into chromosome DNA is described in, for example, Japanese Patent Application Laid-Open No. 1-215280 (1989).

Specifically, the copy number of the gene may be increased by ligating a gene to a multi-copy vector to form a recombinant DNA, and allowing a microorganism to have the recombinant DNA. The vector includes widely used ones such as plasmids and phages, and, in addition to these, transposon (Berg, D. E. and Berg, C. M., Bio/Technol., 1, 417 (1983)) and Mu phage (Japanese Patent Application Laid-Open No. 2-109985 (1990)). It is also possible to integrate a gene into a chromosome by a method utilizing a plasmid for homologous recombination or the like to increase the copy number of the gene.

For breeding a microorganism belonging to the genus *Escherichia* and having an increased expression amount of a gene for an enzyme involved in the purine nucleoside biosynthesis, necessary regions of genes may be obtained by amplified by PCR (polymerase chain reaction) mainly based on already available information about *E. coli* genes, and used for breeding of the microorganism.

For example, purF, which is a gene coding for PRPP amidotransferase, can be cloned from the chromosome DNA of *E. coli* K12 W3110 strain (ATCC27325) using a PCR technique. The chromosome DNA used for this may be derived from any strain of *E. coli*. The purF means a gene coding for PRPP amidotransferase, which is subjected to feedback inhibition by adenosine monophosphate (AMP) or guanosine monophosphate (GMP), and includes mutants generated due to genetic polymorphism and the like. Genetic polymorphism means a phenomenon that an amino acid sequences of a protein is partially altered due to naturally occurring mutation on the gene.

As a means of increasing the activity of the enzyme involved in the purine nucleoside biosynthesis in the cells, it is also possible to introduce a mutation into a structural gene of the enzyme to enhance the enzymatic activity of the enzyme itself.

As a means of increasing the activity of the enzyme involved in the purine nucleoside biosynthesis in the cells, it is also possible to desensitize control of the enzyme involved in the purine nucleoside biosynthesis.

The control of the enzyme involved in the purine nucleoside biosynthesis means a mechanism negatively controlling the activity of the enzyme, and includes feedback inhibition by an intermediate in the biosynthesis pathway or a final product, attenuation, transcriptional suppression and the like. A purine nucleoside produced by a microorganism inhibits the activity of the enzyme involved in the purine nucleoside biosynthesis or represses expression of a gene encoding the enzyme through the control. Therefore, for allowing the microorganism to produce the purine nucleoside, it is preferable to desensitize the control.

The enzyme involved in the purine nucleoside biosynthesis, which undergoes the control, includes PRPP amidotransferase which is subjected to feedback inhibition by AMP or GMP and PRPP synthetase which is subjected to feedback inhibition by adenosine diphosphate (ADP). Besides, inosine monophosphate dehydrogenase (guaB) and GMP synthetase (guaA) are subjected to feedback inhibition by GMP. Also, a purine operon, guaBA is subjected to repression.

As a method for desensitizing the control, a method for introducing mutation into a gene encoding the enzyme or a regulatory region thereof may be mentioned. The mutation includes mutation desensitizing feedback inhibition, which is usually mutation in a structural gene. The mutation also includes mutation desensitizing attenuation, which is usually mutation in attenuator. The mutation also includes mutation desensitizing repression, which is usually mutation in a gene coding a regulatory protein which is called repressor, or mutation in an operator region.

The mutation desensitizing repression includes mutation inactivating a purine repressor. The purine repressor binds to an operator region of a purine operon under the condition that a purine nucleoside exists in a large amount, resulting in repression of transcription of the operon. Inactivation of the repressor leads to desensitization of the repression.

In order to introduce a mutation into a gene, the site-specific mutagenesis (Kramer, W. and Frits, H. J., Methods in Enzymology, 154, 350 (1987)), the recombinant PCR technique (PCR Technology, Stockton Press (1989)), chemical synthesis of a specific portion of DNA, hydroxylamine treatment of a gene of interest, treatment of microbial strains having a gene of interest by UV irradiation or a chemical agent such as nitrosoguanidine or nitrous acid and the like can be used. When function of a gene should be completely inactivated, addition or deletion of DNA may be introduced at a suitable restriction site.

A microorganism in which control of an enzyme involved in the purine nucleoside biosynthesis is desensitized can be selected by determining an expression amount of the enzyme through an enzymatic activity assay, or using antibodies. As an example of a method for obtaining a mutant strain in which control of an enzyme is desensitized, a method comprising selecting a strain growing in a minimal medium containing a purine analogue such as 8-azaadenine and 8-azaguanine, and determining change of an expression amount or activity of the enzyme.

(3) Microorganism which has Acquired the Purine Nucleoside-Producing Ability Because of Blockage of a Reaction Branching from Purine Nucleoside Biosynthesis and Leading to Another Metabolite The purine nucleoside biosynthesis pathway of microorganisms belonging to the genus *Escherichia* has been already elucidated, and all the enzymes involved in the purine nucleoside biosynthesis and reactions catalyzed by those enzymes have also been elucidated (*Escherichia coli* and *Salmonella*, CELLULAR AND MOLECULAR BIOLOGY, Second Edition, vol. 1 and vol. 2, ASM PRESS WASHINGTON D.C.). In addition, some of reactions which lead to other metabolites have also been made clear.

A microorganism in which a reaction leading to another metabolite are blocked may become to require the metabolite. In order to cultivate such microorganism that has become to require the metabolite, it is necessary to add the metabolite or an intermediate (precursor) therefore to a culture medium as a nutrient. Therefore, it is desirable that a reaction not requiring extra addition of the metabolites when it is blocked should be selected as the reaction to be blocked.

The purine nucleoside-producing ability may not be always improved by blocking any of the reactions leading to other metabolites. If a reaction converting a purine nucleoside intermediate or a purine nucleoside into another metabolite proceeds during the production of the purine nucleoside by the microorganism, blocking such a reaction may improve the purine nucleoside productivity.

A reaction whose blocking may actually improve the purine nucleoside-producing ability may be predicted among the reactions branching from the purine nucleoside biosynthesis and leading to the production of another metabolite based on the already elucidated schemes of the purine nucleoside biosynthesis.

As a method for blocking the reaction branching from the purine nucleoside biosynthesis and leading to another metabolite, a method for deleting or inactivating an enzyme catalyzing the reaction or the like may be mentioned. The enzyme may be deleted, for example, by deleting a gene encoding the enzyme. The enzyme may be inactivated by, for example, introducing a mutation into a gene encoding the enzyme, adding an agent specifically inactivating the enzyme or the like.

Examples of the reaction branching from the purine nucleoside biosynthesis and leading to another metabolite, whose blocking may actually improve the purine nucleoside-producing ability, include a reaction catalyzed by an enzyme selected from succinyl-AMP synthase, purine nucleoside phosphorylase, adenosine deaminase, inosine-guanosine kinase, GMP reductase, 6-phosphogluconate dehydrase, phosphoglucose isomerase, adenine deaminase, and xanthosine phosphorylase.

For example, when the branching from IMP to succinyl-AMP and the conversion from inosine to hypoxanthine are blocked, IMP is not converted to AMP and inosine is not converted to hypoxanthine Accordingly, it is expected that inosine is accumulated. In order to evaluate the effectiveness of such blocking, a mutant obtained depending on the purpose may be cultured, and its inosine productivity may be determined.

As described in the Examples hereinafter, when *E. coli* was made adenine auxotrophic by destroying succinyl-AMP synthase gene (purA gene), it became necessary to add an AMP substance such as adenine and adenosine to a culture medium for the growth of the adenine auxotroph of *E. coli*. However, it was found in *E. coli* that such an added substance was immediately converted to inosine or hypoxanthine, and its growth was ceased at a certain point due to the loss of the AMP substance. Therefore, judging from the metabolic pathway of *E. coli*, it is expected that it is necessary to inactivate adenosine deaminase involved in the conversion of adenosine to inosine or adenine deaminase involved in the conversion of adenine to hypoxanthine as a means of maintaining its growth. Thus, the effectiveness of the inactivation of adenosine deaminase or adenine deaminase was confirmed, and accumulation of inosine was observed.

GMP reductase is involved in the conversion of GMP to IMP. It is expected that guanosine productivity is improved by inactivating the GMP reductase As shown in Examples below, a certain level of improvement in guanosine accumulation was observed.

A carbon source such as glucose is used for the production of a purine nucleoside. It is known that there is a difference in sugar metabolic system leading to purine nucleoside biosynthesis depending on the used carbon source or culture conditions. Therefore, for leading the metabolic system to purine nucleoside biosynthesis advantageously, it is considered to block branches other than pentose phosphate pathway to give preference in the pentose phosphate pathway. As a means thereof, inactivation of 6-phosphogluconate dehydrase or phosphoglucose isomerase was tested and the effectiveness thereof was confirmed.

(4) Microorganism which has Acquired the Purine Nucleoside-Producing Ability by Weakening of Incorporation of a Purine Nucleoside into Cells of the Microorganism Since incorporation of a purine nucleoside which has released externally from cells into the cells again is considered unreasonable in view of energy for accumulating the purine nucleoside, weakening of incorporation of a purine nucleoside is effective.

As means of weakening incorporation of a purine nucleoside into cells, blocking of a reaction involved in membrane permeability of the purine nucleoside may be mentioned. The blocking of the reaction can be carried out in the same manner as described about (3) above.

For example, by inactivating nucleoside permease which is one of permeases involved in incorporation of purine nucleosides into cells, improvement in accumulation of inosine was observed.

(5) Method for Producing a Purine Nucleoside

The method for producing a purine nucleoside by fermentation using the microorganism having the purine nucleoside-producing ability is explained hereinafter.

Culture medium for purine nucleoside production to be used may be a usual medium containing a carbon source, a nitrogen source, inorganic ions and other organic components as required. As the carbon source, saccharides such as glucose, lactose, galactose, fructose, arabinose, maltose, xylose, trehalose, ribose and hydrolysates of starches; alcohols such as glycerol, mannitol and sorbitol; organic acids such as gluconic acid, fumaric acid, citric acid and succinic acid and the like can be used. As the nitrogen source, inorganic ammonium salts such as ammonium sulfate, ammonium chloride, and ammonium phosphate; organic nitrogen such as of soy bean hydrolysates; ammonia gas; aqueous ammonia and the like can be used. It is desirable that vitamins such as vitamin B1, required substances, for example, nucleic acids such as adenine and RNA, or yeast extract and the like are contained in appropriate amounts as trace amount organic nutrients. Other than these, small amounts of calcium phosphate, magnesium sulfate, iron ions, manganese ions and the like may be added, if necessary.

Cultivation is preferably performed under an aerobic condition for 16 to 72 hours, and culture temperature during the cultivation is controlled within 30 to 45° C. and pH within 5 to 8. The pH can be adjusted by using an inorganic or organic acidic or alkaline substance as well as ammonia gas.

A purine nucleoside can be recovered from the fermentation liquor by any or any combination of conventional methods such as techniques utilizing ion exchange resin and precipitation.

(6) Specific Examples of Purine Nucleoside-Producing Bacteria

First, purF (a gene coding for PRPP amidotransferase), purR (a gene coding for a purine repressor), deoD (a gene coding for purine nucleoside phosphorylase), purA (a gene coding for succinyl-AMP synthase), add (a gene coding for adenosine deaminase), gsk (a gene coding for inosine-guanosine kinase), guaC (a gene coding for GMP reductase), edd (a gene coding for 6-phosphogluconate dehydrase), pgi (a gene coding for phosphoglucose isomerase), yicP (a gene for coding for adenine deaminase), prs (a gene coding for PRPP synthetase), xapA (a gene coding for xanthosine phosphorylase), and nupG (a gene coding for nucleoside permease) are cloned from a chromosome DNA of *Escherichia coli* (*E. coli*) K12 strain W3110 (ATCC27325) by using a PCR technique, and they may be mutated depending on their purposes. The chromosome DNA used for this procedure may be obtained from any strain of *E. coli*.

The mutation introduced into purF is a mutation for destroying purF or a mutation for desensitizing the feedback inhibition of PRPP amidotransferase. The mutation introduced into purR is a mutation for destroying purR. The mutation introduced into deoD is a mutation for destroying deoD. The mutation introduced into purA is a mutation for destroying purA. The mutation introduced into add is a mutation for destroying add. The mutation introduced into gsk is a mutation for destroying gsk.

The mutation introduced into guaC is a mutation for destroying guaC. The mutation introduced into edd is a mutation for destroying edd. The mutation introduced into pgi is a mutation for destroying pgi. The mutation introduced into yicP is a mutation for destroying yicP. The mutation introduced into prs is a mutation for desensitizing the feedback inhibition of PRPP synthetase. The mutation introduced into xapA is a mutation for destroying xapA. The mutation introduced into nupG is a mutation for destroying nupG.

To introduce a mutation into a gene, the site-specific mutagenesis (Kramer, W. and Frits, H. J., Methods in Enzymology, 154, 350 (1987)), the recombinant PCR technique (PCR Technology, Stockton Press (1989)), chemical synthesis of a specific portion of DNA, hydroxylamine treatment of a gene of interest, treatment of microbial strains having a gene of interest by UV irradiation or a chemical agent such as nitrosoguanidine or nitrous acid and the like can be used. When function of a gene should be completely inactivated, addition or deletion of DNA may be introduced at a suitable restriction site.

Then, purF and prs to which a mutation for desensitizing the feedback inhibition of PRPP amidotransferase and PRPP synthetase are added, respectively, are introduced as a recombinant DNA into a suitable microorganism to express the genes, thereby obtaining a microorganism containing the PRPP amidotransferase gene (purF) and the PRPP synthetase gene (prs) whose feedback inhibition is substantially desensitized. The recombinant DNA obtained above means a vector such as plasmid and phage, into which a useful gene such as the PRPP amidotransferase gene (purF) and the PRPP synthetase (prs) whose feedback inhibition is substantially desensitized is integrated as a passenger. The vector may contain a promoter operable in the microorganism, such as lac, trp, tac, trc, and PL so that efficient expression of the useful gene can be obtained.

The recombinant DNA herein used includes any of those obtained by integrating a useful gene into a chromosome by using a transposon (Berg, D. E. and Berg, C. M., Bio/Technol., 1, 417 (1983)), Mu phage (Japanese Patent Application Laid-Open No. 2-109985 (1990)), a plasmid for homologous recombination or the like.

As the plasmid for homologous recombination, a plasmid having a temperature-sensitive replication origin may be used. The plasmid having the temperature-sensitive replication origin can replicate at a permissive temperature, for example, around 30° C., but cannot replicate at a non-permissive temperature, for example, 37° C. to 42° C. In the homologous recombination method using the plasmid having the temperature-sensitive replication origin, the plasmid can be replicated at a permissive temperature, or dropped out at a non-permissive temperature as required. In the Examples described below, pMAN997, which corresponds to pMAN031 (J. Bacteriol., 162, 1196 (1985)) whose VspI-HindIII fragment is replaced with that of pUC19 (Takara Shuzo) (FIG. 1), was used as the plasmid for homologous recombination.

A specific genetic function on the chromosome was inactivated by the homologous recombination (Experiments in Molecular Genetics, Cold Spring Harbor Lab. (1972)) to improve the purine nucleoside-producing ability. The gene to be inactivated is a gene of which inactivation leads increase of an expression amount of a gene for an enzyme involved in the purine nucleoside biosynthesis. Specifically, the purine repressor gene (purR) on the chromosome was destroyed to remove the expression regulation mechanism of the purine nucleotide biosynthesis genes including the PRPP amidotransferase gene (purF).

Further, a gene coding for an enzyme which catalyzes a reaction branching from purine nucleoside biosynthesis and leading to another metabolite was destroyed. Specifically, the purine nucleoside phosphorylase gene (deoD) was destroyed to suppress the decomposition of inosine and guanosine to hypoxanthine and guanine, respectively. Furthermore, the succinyl-AMP synthase gene (purA) was destroyed to impart adenine auxotrophy. Moreover, the adenosine deaminase gene (add) was destroyed to suppress the conversion of adenosine to inosine. Finally, the inosine-guanosine kinase gene (gsk) was destroyed to suppress the conversion of inosine and guanosine to IMP and GMP, respectively. The GMP reductase gene (guaC) was destroyed to suppress the conversion of GMP to IMP. The 6-phosphogluconate dehydrase gene (edd) was destroyed to suppress metabolism of sugars through the Entner-Doudoroff pathway. The phosphoglucose isomerase gene (pgi) was destroyed to suppress metabolism of sugars through glycolysis pathway, thereby promoting the flow into the pentose phosphate pathway. The adenine deaminase gene (yicP) was destroyed to suppress the conversion of adenine to hypoxanthine. The xantosine phosphorylase gene (xapA) was destroyed to suppress the decomposition of xanthosine to xanthine and to suppress the decomposition of inosine and guanosine to hypoxanthine and guanine, respectively. The inactivation of a target gene may also be performed of course by treatment of microbial strains having the genes with UV irradiation or with a chemical agent such as nitrosoguanidine and nitrous acid.

As the microorganism having the recombinant DNA, a microorganism belonging to the genus Escherichia in which a gene coding for a target enzyme such as PRPP amidotransferase was expressed was used.

In order to efficiently utilize the PRPP amidotransferase gene (purF), it is preferably used together with other useful genes, for example, genes involved in the IMP biosynthesis from PRPP other than purF (purD, purT, purL, purM, purK, purE, purC, purB, purH), IMP dehydrogenase gene (guaB), GMP synthetase gene (guaA), PRPP synthetase gene (prs) and the like. Like the PRPP amidotransferase gene (purF), those useful genes may be present on a host chromosome, or a plasmid or phage.

A microorganism having deficiency of purA (succinyl-AMP synthase gene) and/or deficiency of deoD (purine nucleoside phosphorylase gene) and/or deficiency of purR (purine repressor gene) and/or desensitized type purF (PRPP amidotransferase gene) and/or deficiency of add (adenosine deaminase gene) and/or deficiency of gsk (inosine-guanosine kinase gene) and/or deficiency of guaC (GMP reductase gene) and/or deficiency of edd (6-phosphogluconate dehydrase gene) and/or deficiency of pgi (phosphoglucose isomerase gene) and/or deficiency of yicP (adenine deaminase gene) and/or deficiency of xapA (xanthosine phosphorylase gene) and/or deficiency of nupG (nucleoside permease gene), or a microorganism transformed with a recombinant DNA having desensitized type PRPP amidotransferase gene (purF) and/or desensitized type prs (PRPP synthetase gene) obtained as described above is cultured so that the target purine nucleoside such as inosine and guanosine is accumulated in the culture medium, and the accumulated nucleoside is collected.

BEST MODE FOR CARRYING OUT THE INVENTION

Example 1

1) Breeding of Strain Deficient in PRPP Amidotransferase Gene (purF)

PCR was carried out (94° C., 30 sec; 55° C., 1 min; 72° C., 2 min; 30 cycles; GeneAmp PCR System Model 9600, Perkin Elmer) by using chromosome DNA of E. coli K12 strain W3110 (ATCC27325) as a template and 29-mer and 31-mer primers for both ends, having nucleotide sequences of CTC-CTGCAGAACGAGGAAAAAGACGTATG (SEQ ID NO: 1) and CTCAAGCTTTCATCCTTCGTTATGCATTTCG (SEQ ID NO: 2), and prepared based on the information of a gene data bank (GenBank Accession No. M26893), and an amplified fragment of about 1530 bp of the purF structural gene region covering SD-ATG and the translation termination codon was cloned into pCRTMII vector (Invitrogen). The amplified fragment of the PCR product can be cloned into this vector as it is. The vector has EcoRI sites as restriction sites at vicinities of the both sides of the cloning site. A PstI site and a HindIII site are respectively provided in the PCR primers.

Figure 2:
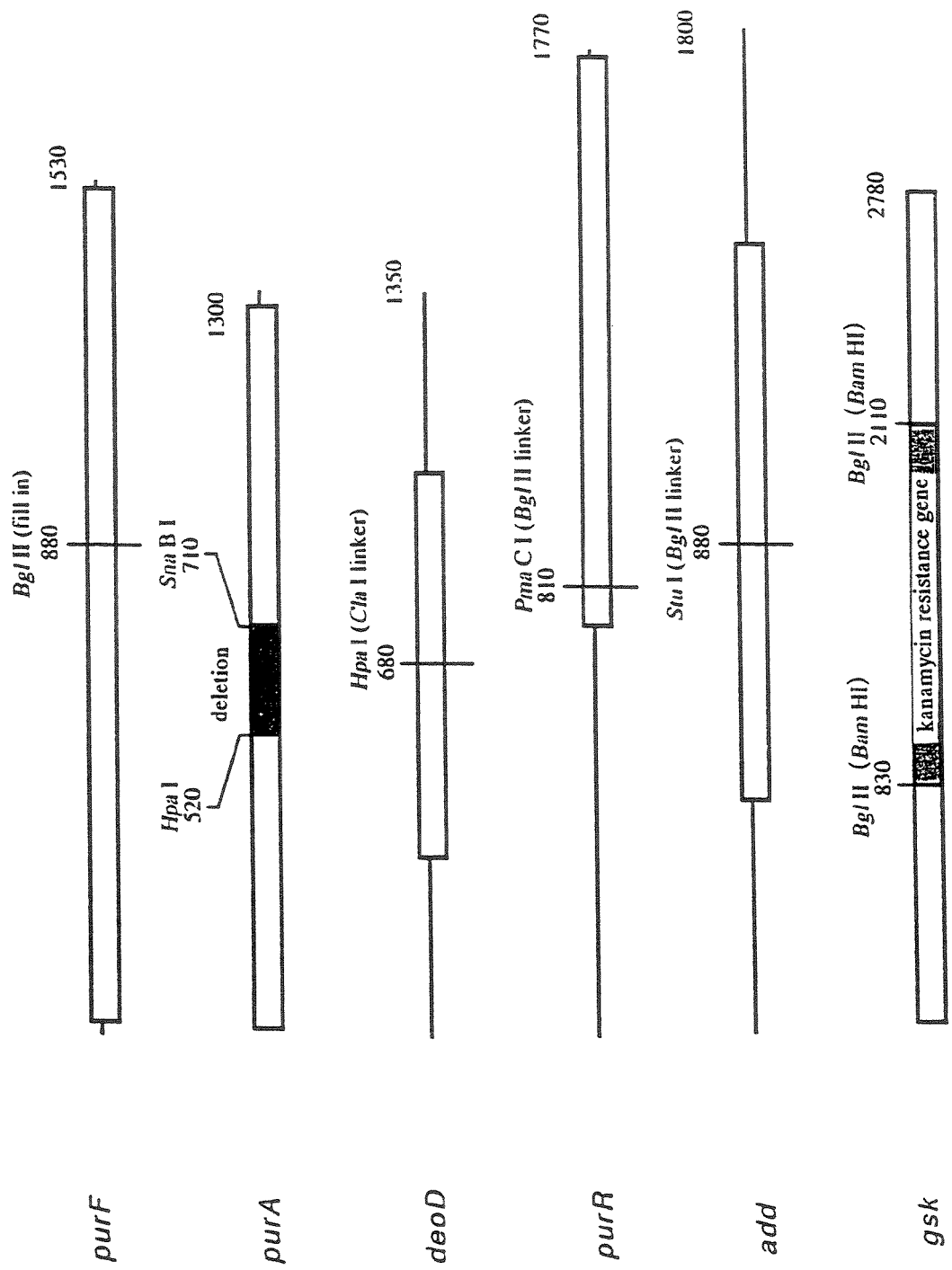
FIG. 2 shows structures of genes for homologous recombination. Numerals in the figure represent lengths (bp) of obtained fragments and positions from 5' ends.

The cloned 1530 bp purF fragment contained one BglII site at about 880 bp from the 5' end, and pCRTMII vector itself also had one BglII site. Therefore, the plasmid was partially digested with BglII, blunt-ended by T4 DNA polymerase, and then ligated by T4 DNA ligase. Competent cells of E. coli HB101 were transformed with this ligation solution, and transformants grown on LB (1% tryptone, 0.5% yeast extract, 0.1% NaCl, 0.1% Glucose, pH 7) agar plates containing 25 μg/ml of ampicillin were obtained. Plasmid DNAs were prepared from the transformants of 18 clones, and a plasmid DNA which provided a fragment of about 1550 bp by the EcoRI digestion, which fragment was not digested with BglII (pCRTMIIpurF'#14) was selected from the plasmid DNAs. The purF contained in this plasmid DNA has a frame shift at the BglII site, and therefore it is predicted that the encoded enzyme lacks its function (FIG. 2).

Figure 1:
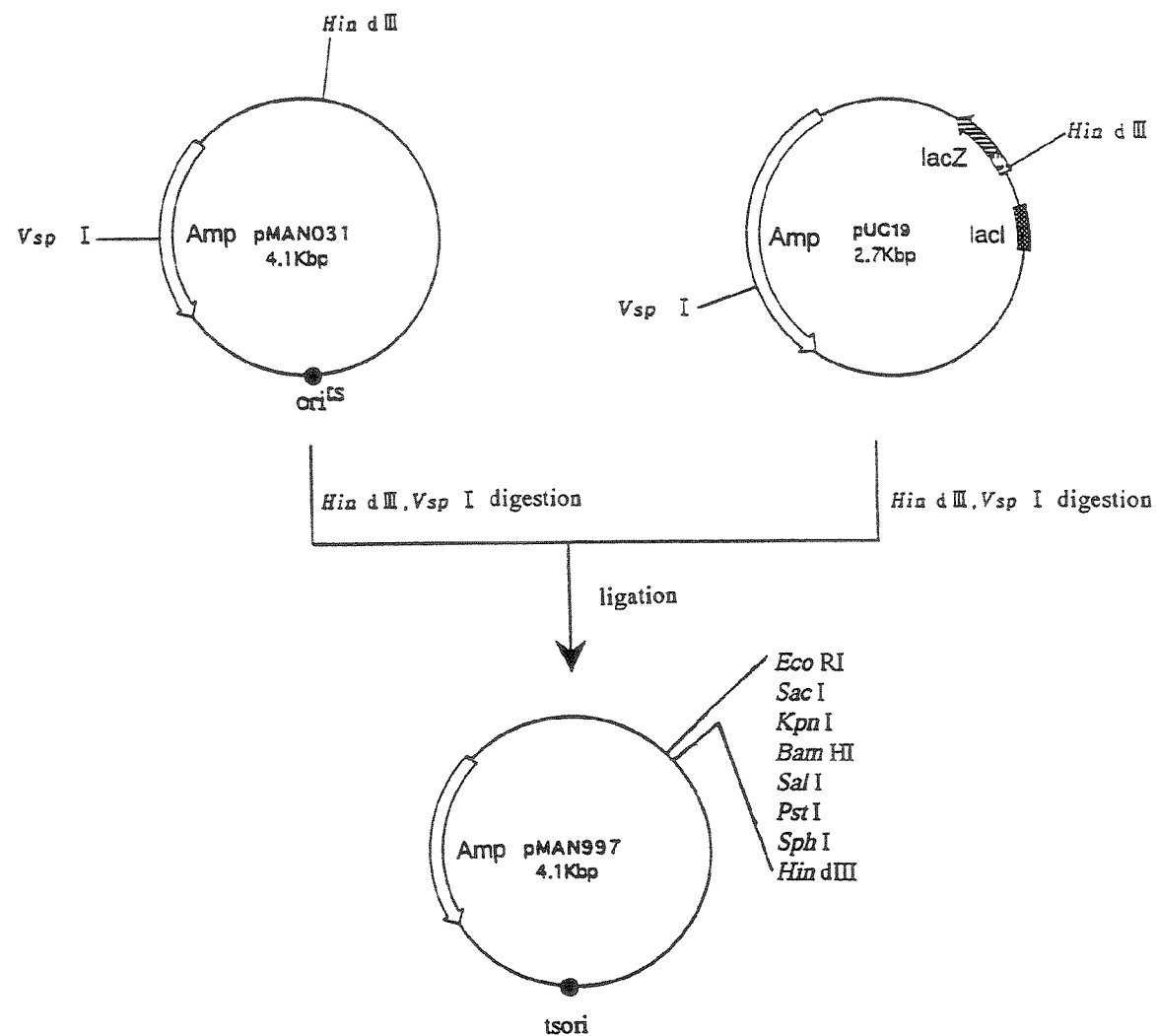
FIG. 1 shows a construction of pMAN997.

Then, the pCRTMIIpurF'#14 was digested with EcoRI to prepare a fragment of about 1.6 Kb that included the purF. This fragment was inserted into the EcoRI site of pMAN997, which is a vector for homologous recombination having a temperature-sensitive replication origin (tsori) (As shown in FIG. 1, pMAN031 (J. Bacteriol., 162, 1196 (1985)) of which VspI-HindIII fragment is replaced with that of pUC19 (Takara Shuzo)), to obtain plasmid pMAN997purF'#14. E. coli W3110 (wild type) was transformed at 30° C. with the pMAN997purF'#14, and some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture broth was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. Among the ampicillin-sensitive clones, clones that were not grown in a minimal medium ($Na_2HPO_4$ 6.8 g, $KH_2PO_4$ 3 g, NaCl 0.5 g, $NH_4Cl$ 1 g, $MgSO_4 \cdot 7H_2O$ 0.5 g, $CaCl_2 \cdot 2H_2O$ 15 mg, thiamin-HCl 2 mg, glucose 0.2 g per 1 L), but grown in the minimal medium supplemented with 50 mg/L of hypoxanthine were further selected. Furthermore, the fragment of about 1.5 kb including purF was amplified by PCR from the chromosome DNA of the above obtained target clones, and confirmed not to be digested with BglII. The clones satisfying the above conditions were considered strains deficient in purF, and designated as strains F-2-51 and F-1-72.

2) Breeding of Strain Deficient in Succinyl-AMP Synthase Gene (purA)

PCR was carried out (94° C., 30 sec; 55° C., 1 min; 72° C., 2 min; 30 cycles; Gene Amp PCR system Model 9600, Perkin Elmer) by using the chromosome DNA of the strain W3110 as a template and 31-mer primers for both ends, having nucleotide sequences of CTCGAGCTCATGGGTAA-CAACGTCGTCGTAC (SEQ ID NO: 3) and CTCGTC-GACTTACGCGTCGAACGGGTCGCGC (SEQ ID NO: 4), and prepared based on the information of a gene data bank (GenBank Accession No. J04199), and an amplified fragment of about 1300 bp of the purA structural gene region covering ATG and the translation termination codon was cloned between the SacI and SalI sites of pUC18 vector (Takara Shuzo). A SacI site and a SalI site are respectively provided in the PCR primers. The cloned purA fragment of about 1300 bp contained one HpaI site and one SnaBI site respectively at about 520 bp and 710 bp from the 5' end, and therefore the plasmid was digested with HpaI and SnaBI, and ligated by T4 DNA ligase to obtain the plasmid from which a fragment of about 190 bp was removed. Competent cells of *E. coli* JM109 were transformed with this ligation solution, and transformants grown on LB agar plates containing 25 µg/ml of ampicillin were obtained. Plasmid DNAs were prepared from the transformants of 18 clones, and a plasmid DNA that was not digested with FspI but provided a fragment of about 1100 bp fragment by SacI and SalI digestion (pUC18purA'#1) was selected from the plasmid DNAs. The purA contained in this plasmid DNA has a deletion between the HpaI and SnaBI sites, and therefore it is predicted that the encoded enzyme lacks its function (FIG. 2).

Then, the pUC18purA'#1 was digested with SacI and SalI to prepare a fragment of about 1.1 kb that included the purA. This fragment was inserted between the SacI and SalI sites of pMAN997, which is a vector for homologous recombination having a temperature-sensitive replication origin (tsori) (described above), to obtain plasmid pMAN997purA'#1. The strain F-2-51 (purF⁻) was transformed at 30° C. with the plasmid pMAN997purA'#1, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture broth was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. Among the ampicillin-sensitive clones, clones that were not grown on the minimal medium supplemented with 50 mg/L of hypoxanthine, but grown on the minimal medium supplemented with 50 mg/L of adenine were further selected. Furthermore, the purA fragment of about 1.1 kb was amplified by PCR from the chromosome DNA of these target clones, and confirmed to be smaller than the wild type (about 1.3 kb) and not to be digested with FspI. The clone satisfying the above conditions was considered a strain deficient in purA, and designated as strain FA-31.

3) Breeding of Strain Deficient in Purine Nucleoside Phosphorylase Gene (deoD)

PCR was carried out (94° C., 30 sec; 55° C., 1 min; 72° C., 2 min; 30 cycles; Gene Amp PCR System Model 9600, Perkin Elmer) by using the chromosome DNA of the strain W3110 as a template and 30-mer and 31-mer primers for both ends, having nucleotide sequences of CTCGTC-GACGCGGGTCTGGAACTGTTCGAC (SEQ ID NO: 5) and CTCGCATGCCCGTGCTTTACCAAAGCGAATC (SEQ ID NO: 6), and prepared based on the information obtained through searching of a gene data bank (*E. coli* Gene Bank) using "deoD" as a key word, and an amplified fragment of about 1350 bp including a deoD structural gene region covering SD-ATG and the translation termination codon was cloned into pCRTMII vector (Invitrogen). The vector has EcoRI sites as restriction sites at vicinities of the both sides of the cloning site. A SalI site and a SphI site are respectively provided in the PCR primers. The cloned deoD fragment of about 1350 bp contained one HpaI site at about 680 bp from the 5' end, and therefore the plasmid was digested with HpaI, and a mixture of the digested plasmid and a 10-mer ClaI linker was subjected to T4 DNA ligase reaction. As a result, a ClaI site was inserted at the HpaI site. Competent cells of *E. coli* HB101 were transformed with this ligation solution, and transformants grown on LB agar plates containing 25 µg/ml of ampicillin were obtained. Plasmid DNAs were prepared from the transformants of 16 clones, and a plasmid DNA that was not digested with HpaI but digested with ClaI (pCRTMIIdeoD'#16) was selected from the plasmid DNAs. The deoD contained in this plasmid has a frame shift at the HpaI site, and therefore it is predicted that the encoded enzyme lacks its function (FIG. 2).

Then, the pCRTMIIdeoD'#16 was digested with EcoRI to prepare a fragment of about 1.35 kb that included the deoD. This fragment was inserted into the EcoRI site of pMAN997, which is a vector for homologous recombination having a temperature-sensitive replication origin (tsori) (described above), to obtain plasmid pMAN997deoD'#16. The strain F-1-72 (purF⁻) and the strain FA-31 (purF⁻, purA⁻) were transformed at 30° C. with plasmid pMAN997deoD'#16, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture broth was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. The ampicillin-sensitive clones were allowed to row on the LB medium supplemented with 1 g/L of inosine, and clones that did not decompose inosine to hypoxanthine were selected through thin layer chromatography analysis of the culture medium. Furthermore, the fragment of about 1.35 kb including deoD was amplified by PCR from the chromosome DNA of these target clones, and confirmed to be digested with ClaI but not to be digested with HpaI. The clones satisfying the above conditions were considered strains deficient in deoD, and clones derived from the strain F-1-72 (purF$^-$) and the strain FA-31 (purF$^-$, purA$^-$) were designated as strains FD-6 and FAD-25, respectively.

4) Breeding of Strain Deficient in Purine Repressor Gene (purR)

PCR was carried out (94° C., 30 sec; 55° C., 1 min; 72° C., 2 min; 30 cycles; GeneAmp PCR System Model 9600, Perkin Elmer) by using the chromosome DNA of the strain W3110 as a template and 29-mer and 28-mer primers for both ends, having nucleotide sequences of CTCGTCGACGAAAGTA-GAAGCGTCATCAG (SEQ ID NO: 7) and CTCGCATGCT-TAACGACGATAGTCGCGG (SEQ ID NO: 8), and prepared based on the information obtained through searching of a gene data bank (*E. coli* Gene Bank) using "purR" as a key word, and an amplified fragment of about 1.8 kb including a purR structural gene region covering ATG and the translation termination codon and about 800 bp 5' upstream region of ATG was cloned between the SalI site and the SphI site of pUC19 vector (Takara Shuzo). A SalI site and a SphI site are respectively provided in the PCR primers, and these sites are used for cloning. The cloned purR fragment of about 1.8 kb contained one PmaCI site at about 810 bp from the 5' end (vicinity of N-terminus in the purR structural gene region), and therefore the plasmid was digested with PmaCI. A mixture of the digested plasmid and a 8-mer BglII linker was subjected to T4 DNA ligase reaction. As a result, a BglII site was inserted at the PmaCI site. Competent cells of *E. coli* JM109 were transformed with this ligation solution, and transformants grown on LB agar plates containing 25 µg/ml of ampicillin were obtained. Plasmid DNAs were prepared from the transformants of 10 clones, and a plasmid DNA not digested with PmaCI but digested with BglII (pUC19purR'#2) was selected from the plasmid DNAs. The purR contained in this plasmid DNA has a frame shift at the PmaCI site, and therefore it is predicted that the encoded enzyme lacks its function (FIG. 2).

Then, the pUC19purR' #2 was digested with SacI and SphI to prepare a fragment of about 1.8 kb that included the purR. This fragment was inserted between the SacI site and the SphI site of pMAN997, which is a vector for homologous recombination having a temperature-sensitive replication origin (tsori) (described above), to obtain plasmid pMAN997purR'#2. The strain FD-6 (purF$^-$, deoD$^-$) and the strain FAD-25 (purF$^-$, purA$^-$, deoD$^-$) were transformed at 30° C. with the plasmid pMAN997purR'#2, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain single colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture broth was appropriately diluted so that single colonies should be obtained (about 10$^{-5}$ to 10$^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. Ten clones were randomly selected from the ampicillin-sensitive clones, and the fragment of about 1.8 kb including purR was amplified by PCR from the chromosome DNA of these clones, and clones that were digested with Bgl II but not with PmaCI were selected. These clones were considered strains deficient in purR, and clones derived from the strain FD-6 (purF$^-$, deoD$^-$) and the strain FAD-25 (purF$^-$, purA$^-$, deoD$^-$) are designated as strain FDR-18 and strain FADR-8, respectively. It was confirmed that the PRPP amidotransferase activity in the strains in which purR was destroyed was increased compared with that of a strain in which purR was not destroyed by using the purF$^+$ strain deficient in deoD and purR or the purF$^+$ strain deficient in purA, deoD and purR. The PRPP amidotransferase activity was measured according to the method of L. J. Messenger et al. (J. Biol. Chem., 254, 3382 (1979)).

5) Construction of Desensitized Type PRPP Amidotransferase Gene (purF)

A purF fragment was excised from the plasmid carrying the purF of about 1530 bp cloned into pCRTMII vector (Invitrogen) in Section 1) by digestion with PstI and HindIII, and inserted between the PstI and HindIII sites of the multi-cloning site of a plasmid for introducing mutation, pKF18 (Takara Shuzo) to obtain the target clone (pKFpurF). G. Zhou et al. (J. Biol. Chem., 269, 6784 (1994)) has revealed that PRPP amidotransferase (PurF) whose Lys (K) at position 326 is replaced with Gln (Q) and the same whose Pro (P) at position 410 is further replaced with Trp (W) are each desensitized for feedback inhibition by GMP and AMP. Therefore, the following synthetic DNA primers were prepared for gene substitution realizing mutations of Lys (K) at position 326 and Pro (P) at position 410 of PRPP amidotransferase (PurF) to Gln (Q) and Trp (W), respectively, and pKFpurF was subjected to site-directed mutagenesis according to the protocol of Site-directed Mutagenesis System Mutan-Super Express Km (Takara Shuzo) to introduce a site-directed mutation into the pKFpurF.

```
Primer for K326Q mutation:
                                      (SEQ ID NO:9)
5'-GGGCTTCGTT CAG AACCGCTATGTTGG-3'

Primer for P410W mutation:
                                     (SEQ ID NO:10)
5'-TATGGTATTGATATG TGG AGCGCCACGGAAC-3'
```

After the mutagenesis, 6 clones were randomly picked up from each of the resulting transformants, and plasmids were prepared from them. By nucleotide sequencing of the plasmids around the locations where the mutations were introduced, it was confirmed that target mutants were obtained. The obtained plasmids were designated as pKFpurFKQ and pKFpurFPW, respectively. The mutation P410W (410Pro→Trp) was further introduced into pKFpurFKQ in the same manner to prepare pKFpurFKQPW, a mutant plasmid having two mutations simultaneously. Each of the plasmids pKFpurFKQ, pKFpurFPW and pKFpurFKQPW has an inserted mutant purF downstream of the lacp/o (promoter of lactose operon) derived from pKF18, and the purF is expressed under the control of this promoter.

Recombinant bacteria obtained by transforming *E. coli* JM109 cells with the above plasmids were cultured in LB liquid medium for eight hours, and collected, and crude enzyme extracts were prepared from them. The PRPP amidotransferase activity of the extracts and degrees of inhibition by AMP and GMP were measured according to the method of L. J. Messenger (J. Biol. Chem., 254, 3382 (1979)). The results are shown in Table 1.

TABLE 1

PRPP amidotransferase activity and inhibition by AMP and GMP

| | | PRPP amidotransferase activity (μmole/min/mg) | | |
|---|---|---|---|---|
| Host | Plasmid | None | 10 mM AMP | 10 mM GMP |
| JM109 | — | 0.001 | — | — |
| JM109 | pKFpurF | 0.68 | 0.48 | 0.10 |
| JM109 | pKFpurFKQ | 0.34 | 0.32 | 0.33 |
| JM109 | pKFpurFKQPW | 0.18 | 0.16 | 0.17 |

6) Evaluation of Purine Nucleoside-Producing Ability of Mutant purF Plasmid-Introduced Strain Transformants were produced by introducing pKFpurFKQ and pKFpurFKQPW into the strain FDR-18 (purF$^-$, deoD$^-$, purR$^-$) and the strain FADR-8 (purF$^-$, purA$^-$, deoD$^-$, purR$^-$) produced in Section 4), and purine nucleoside-producing abilities of these strains were evaluated.

Basal medium and culture method for purine nucleoside production and analysis method for the evaluation of the purine nucleoside-producing ability will be described below.

1. Basal Medium: MS Medium

| | Final concentration |
|---|---|
| Glucose | 40 g/L (separately sterilized) |
| (NH$_4$)$_2$SO$_4$ | 16 g/L |
| KH$_2$PO$_4$ | 1 g/L |
| MgSO$_4$•7H$_2$O | 1 g/L |
| FeSO$_4$•7H$_2$O | 0.01 g/L |
| MnSO$_4$•4H$_2$O | 0.01 g/L |
| Yeast extract | 2 g/L |
| CaCO$_3$ | 30 g/L (separately sterilized) |

2. Culture Method
Refresh Culture; a Stored Bacterium Inoculated
    LB agar medium (supplemented with a drug as required)
    37° C., cultured overnight.
Seed Culture; the Refresh Cultured Bacterium Inoculated
    LB liquid medium (supplemented with a drug as required)
    37° C., cultured overnight.
Main Culture; 2% Inoculated from the Seed Culture
    MS medium (supplemented with adenine and a drug as required)
    37° C., 20 ml/500-ml volume Sakaguchi's culture flask 3. Analysis Method
A sample of the culture medium (500 μl) is repeatedly taken in the time course, and centrifuged at 15,000 rpm for 5 minutes, and the supernatant is diluted 4 times with H$_2$O and analyzed by HPLC. Unless noted otherwise, the evaluation is made based on an accumulated amount of a purine nucleoside per unit volume of the medium after culture for 3 days.
Analysis Conditions:
Column: Asahipak GS-220 (7.6 mm ID×500 mm L)
Buffer: pH is adjusted with 0.2M NaH$_2$PO$_4$ (pH 3.98), and phosphoric acid
Temperature: 55° C.
Flow Rate: 1.5 ml/min
Detection: uv 254 nm
Retention time (min)

| | |
|---|---|
| Inosine | 16.40 |
| Hypoxanthine | 19.27 |
| Guanosine | 20.94 |
| Guanine | 23.55 |
| Adenine | 24.92 |
| Adenosine | 26.75 |

For the strains of purA$^-$ (adenine auxotrophic), 5 mg/L of adenine was added to the MS medium.

The results of the evaluation of the purine nucleoside-producing ability are shown in Table 2. Superior inosine production was observed with respect to the mutant purF plasmid-introduced strains in contrast to the strain W3110 (wild type strain) by which a trace amount of the production was observed.

TABLE 2

Evaluation of purine nucleoside-producing ability

| | | Purine nucleoside accumulation | |
|---|---|---|---|
| Host | Plasmid | Inosine (mg/L) | Guanosine (mg/L) |
| W3110 | — | Trace | 0 |
| FDR-18 | pKFpurFKQ | 115 | 0 |
| FDR-18 | pKFpurFKQPW | 110 | 0 |
| FADR-8 | pKFpurFKQ | 66 | 0 |
| FADR-8 | pKFpurFKQPW | 62 | 0 |

Example 2

1) Breeding of Strain Deficient in Adenosine Deaminase Gene (add)

PCR was carried out (94° C., 30 sec; 55° C., 1 min; 72° C., 2 min; 30 cycles; Gene Amp PCR System Model 9600, Perkin Elmer) by using the chromosome DNA of the strain W3110 as a template and 29-mer primers for both ends, having nucleotide sequences of CTCGTCGACGGCTGGATGCCT-TACGCATC (SEQ ID NO: 11) and CTCGCATGCAGT-CAGCACGGTATATCGTG (SEQ ID NO: 12), and prepared based on the information obtained through searching of a gene data bank (*E. coli* Gene Bank) using "add" as a key word, and an amplified fragment of about 1.8 kb including an add structural gene region covering ATG and the translation termination codon, about 420 bp 5' upstream region of ATG and about 370 bp downstream region of the translation termination codon was cloned between the SalI site and the SphI site of pUC19 vector (Takara Shuzo). A SalI site and a SphI site are respectively provided in the PCR primers, and these sites are used for the cloning. The cloned add fragment of about 1.8 kb contained one StuI site at about 880 bp from the 5' end, and therefore the plasmid was digested with StuI, and a mixture of the digested plasmid and a 8-mer BglII linker was subjected to T4 DNA ligase reaction. As a result, a Bgl II site was inserted at the StuI site Competent cells of *E. coli* JM109 were transformed with this ligation solution, and transformants grown on LB agar plates containing 25 µg/ml of ampicillin were obtained Plasmid DNAs were prepared from the transformants of 10 clones, and a plasmid DNA not digested with StuI but digested with BglII (pUC19add'#1) was selected from the plasmid DNAs. The add contained in this plasmid DNA has a frame shift at the StuI site, and therefore it is predicted that the encoded enzyme lacks its function (FIG. 2).

Then, the pUC19add'#1 was digested with SacI and SphI to prepare a fragment of about 1.8 kb that included the add. This fragment was inserted between the SacI site and the SphI site of pMAN997, which is a vector for homologous recombination having a temperature-sensitive replication origin (tsori) (described above), to obtain plasmid pMAN997add'#1. The strain FDR-18 (purF$^-$, deoD$^-$, purR$^-$) and the strain FADR-8 (purF$^-$, purA$^-$, deoD$^-$, purR$^-$) were transformed at 30° C. with the plasmid pMAN997add'#1, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking The culture broth was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. The ampicillin-sensitive clones were allowed to grow in the LB medium supplemented with 1.5 g/L of adenosine, and clones that did not convert adenosine to inosine were selected through thin layer chromatography analysis of the culture medium. Furthermore, the add fragment of about 1.8 kb was amplified by PCR from the chromosome DNA of these target clones, and confirmed to be digested with BglII but not to be digested with StuI. These clones were considered strains deficient in add, and clones derived from the strain FDR-18 (purF$^-$, deoD$^-$, purR$^-$) and the strain FADR-8 (purF$^-$, purA$^-$, deoD$^-$, purr) are designated as strains FDRadd-18-1 and FADRadd-8-3, respectively.

2) Evaluation of Purine Nucleoside-Producing Ability of Desensitized Type purF-Introduced Strain Transformants were made by introducing pKFpurFKQ and pKFpurFKQPW into the strain FDRadd-18-1 (purF$^-$, deoD$^-$, purR$^-$, add$^-$) and the strain FADRadd-8-3 (purF$^-$, purA$^-$, deoD$^-$, purR$^-$, add$^-$) bred in Section 1), and purine nucleoside-producing abilities of these strains were evaluated. For the strain FADRadd-8-3, a transformant with the wild type purF plasmid (pKFpurF) was also made, and compared with the transformant with pKFpurFKQ and the transformant with pKFpurFKQPW. The basal medium and the culture method for the purine nucleoside production and the analysis method were the same as Example 1.

The results of the evaluation of the purine nucleoside-producing ability are shown in Table 3. Superior inosine production was observed compared with the strain W3110 (wild type strain). Effects of desensitized type purFKQ and purFKQPW were observed by comparing with the wild type purF.

TABLE 3

Evaluation of purine nucleoside-producing ability

| | | Purine nucleoside accumulation | |
|---|---|---|---|
| Host | Plasmid | Inosine (mg/L) | Guanosine (mg/L) |
| W3110 | — | Trace | 0 |
| FDRadd-18-1 | pKFpurFKQ | 220 | 0 |
| FDRadd-18-1 | pKFpurFKQPW | 215 | 0 |
| FADRadd-8-3 | pKFpurFKQ | 1080 | 0 |
| FADRadd-8-3 | pKFpurFKQPW | 1030 | 0 |
| FADRadd-8-3 | pKFpurF | 805 | 0 |

Example 3

1) Construction of Desensitized Type purF Plasmid for Homologous Recombination

In order to introduce desensitized type purF substitution in a chromosome by using the purF$^-$ strain produced in Example 1, Section 1), another purF fragment longer than the previously obtained purF fragment (about 1.6 kb) by about 0.5 kb for the 3' side was prepared. PCR was carried out (94° C., 30 sec; 55° C., 1 min; 72° C., 2 min; 30 cycles; Gene Amp PCR System Model 9600, Perkin Elmer) by using the chromosome DNA of the strain W3110 and 29-mer primers for both ends, having nucleotide sequences of CTCCTGCAGAACGAG-GAAAAAGACGTATG (SEQ ID NO: 1) and CTCAAGCT-TGTCTGATTTATCACATCATC (SEQ ID NO: 13), and prepared based on the information of the gene data bank (*E. coli* Gene Bank), and an amplified fragment of about 2.1 kb including the purF structural gene region covering SD-ATG and the translation termination codon was cloned into pCRT-MII vector (Invitrogen). The plasmid contained in this clone is designated as pCRTMIIpurFL. The pCRTMIIpurFL has EcoRI sites as restriction sites at vicinities of the both sides of the cloning site. A PstI site and a HindIII site are respectively provided in the PCR primers.

Then, the pCRTMIIpurFL was digested with SnaBI and HindIII to obtain a fragment of about 0.65 kb present downstream of the C-terminus of the purF coding region This fragment was inserted between the SnaBI site and the HindIII site of pKFpurFKQ and pKFpurFKQPW obtained in Example 1, Section 5) to obtain pKFpurFLKQ and pKFpurFLKQPW.

Then, the pKFpurFLKQ and pKFpurFLKQPW were digested with EcoRI and HindIII to give fragments of about 2.1 kb containing purFLKQ and purFLKQPW. These fragments were inserted between the EcoRI and HindIII sites of pMAN997, which is a vector for homologous recombination having a temperature-sensitive replication origin (tsori) (described above), to obtain plasmids pMAN997purFLKQ and pMAN997purFLKQPW, respectively.

2) Breeding of Strain Having Desensitized Type purF Integrated in Chromosome

The strain FDRadd-18-1 (purF⁻, deoD⁻, purR⁻, add⁻) and the strain FADRadd-8-3 (purF⁻, purA⁻, deoD⁻, purR⁻, add⁻) were each transformed with the plasmids pMAN997purFLKQ and pMAN997purFLKQPW at 30° C., and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. Among the ampicillin-sensitive clones, clones that were grown on the minimal medium were selected for the strain FDRadd-18-1 (purF⁻, deoD⁻, purR⁻, add⁻), and clones that were grown in the minimal medium supplemented with 100 mg/L of L-histidine and 50 mg/L of adenine were selected for the strain FADRadd-8-3 (purF⁻, purA⁻, deoD⁻, purR⁻, add⁻).

The fragments of about 1.5 kb including purF were amplified from chromosome DNA of these target clones, and nucleotide sequences around the locations where mutations were introduced by homologous recombination substitution were determined. As a result, it was confirmed that they contained the mutation of K326Q (326Lys→Gln), and the mutations of K326Q (326Lys→Gln)+P410W (410Pro→Trp), respectively.

Those derived from the strain FDRadd-18-1 (purF⁻, deoD⁻, purR⁻, add⁻) were designated as strain FDRadd-18-1::KQ (purFKQ, deoD⁻, purR⁻, add⁻) and strain FDRadd-18-1::KQPW (purFKQPW, deoD⁻, purR⁻, add⁻), and those derived from the strain FADRadd-8-3 (purF⁻, purA⁻, deoD⁻, purR⁻, add⁻) were designated as strain FADRadd-8-3::KQ (purFKQ, purA⁻, deoD⁻, purR⁻, add⁻) and strain FADRadd-8-3::KQPW (purFKQPW, purA⁻, deoD⁻, purR⁻, add⁻).

3) Evaluation of Purine Nucleoside-Producing Ability of Strain Having Desensitized Type purF Integrated into Chromosome Purine nucleoside-producing abilities of the strain FDRadd-18-1::KQ (purFKQ, deoD⁻, purR⁻, add⁻), the strain FDRadd-18-1::KQPW (purFKQPW, deoD⁻, purR⁻, add⁻), the strain FADRadd-8-3::KQ (purFKQ, purA⁻, deoD⁻, purR⁻, add⁻) and the strain FADRadd-8-3::KQPW (purFKQPW, purA⁻, deoD⁻, purR⁻, add⁻) prepared in Section 2) were evaluated. The basal medium and the culture method for the purine nucleoside production and the analysis method were the same as Example 1. For the strains of purA⁻ (adenine auxotrophic), 5 mg/L of adenine was added to the MS medium.

The results of the evaluation of purine nucleoside-producing ability are shown in Table 4. Superior inosine production was observed compared with the strain W3110 (wild type strain).

TABLE 4

Evaluation of purine nucleoside-producing ability

| Strain | Purine nucleoside accumulation | |
|---|---|---|
| | Inosine (mg/L) | Guanosine (mg/L) |
| W3110 | Trace | 0 |
| FDRadd-18-1::KQ | 110 | 0 |
| FDRadd-18-1::KQPW | 105 | 0 |
| FADRadd-8-3::KQ | 635 | 0 |
| FADRadd-8-3::KQPW | 620 | 0 |

Example 4

1) Breeding of Strain Deficient in Inosine-Guanosine Kinase Gene (gsk)

PCR was carried out (94° C., 30 sec; 55° C., 1 min; 72° C., 2 min; 30 cycles; GeneAmp PCR System Model 9600, Perkin Elmer) by using the chromosome DNA of the strain W3110 and 23-mer and 21-mer primers for both ends, having nucleotide sequences of CTCGAGCTCATGAAATTTCCCGG (SEQ ID NO: 14) and CTCGGATCCGGTACCATGCTG (SEQ ID NO: 15), and prepared based on the information of a gene data bank (GenBank Accession No. D00798), and an amplified fragment of about 1.5 kb including the gsk structural gene region covering ATG and the translation termination codon was cloned between the SacI site and the BamHI site of pUC18 vector (Takara Shuzo). A SacI site and a BamHI site are respectively provided in the PCR primers.

The cloned gsk fragment of 1.5 kb contained one BglII site at about 830 bp from the 5 end, and therefore the plasmid was digested with BglII, and subjected to T4 DNA ligase reaction in order to insert a kanamycin resistant (Km$^r$) gene GenBlock (BamHI digest, Pharmacia Biotech). Competent cells of *E. coli* JM109 were transformed with this ligation solution, and transformants grown on LB agar plates containing 50 µg/ml of kanamycin were obtained. Plasmid DNAs were prepared from the transformants of 4 clones, and a plasmid DNA that was not digested with BglII from which plasmid a fragment of about 2.8 kp was excised by EcoRI and SalI digestion (pUCgsk'#2) was selected from the plasmid DNAs. The gsk contained in this plasmid has an inserted heterogeneous gene at the BglII site, and therefore it is predicted that the encoded enzyme lacks its function (FIG. 2).

Then, the pUCgsk'#2 was digested with SacI, SphI and DraI to prepare a fragment of about 2.8 Kb that included the gsk and Km$^r$ genes. The DraI digestion is employed to facilitate the preparation of a SacI-SphI fragment. The fragment was inserted between the SacI and SphI sites of pMAN997, which is a vector for homologous recombination having a temperature-sensitive replication origin (tsori) (describe above), to obtain plasmid pMAN997gsk'#2. The strain FDR-18 (purF⁻, deoD⁻, purR⁻) and the strain FADRadd-8-3 (purF⁻, purA⁻, deoD⁻, purR⁻, add⁻) were transformed at 30° C. with the plasmid pMAN997gsk'#2, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C.

The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates, LB agar plates containing 25 μg/ml of ampicillin, respectively, and LB agar plates containing 20 μg/ml of kanamycin, respectively, and clones not grown on the LB agar plates containing 25 μg/ml of ampicillin, but grown on the LB agar plates containing 20 μg/ml of kanamycin were selected. Furthermore, the fragment including the gsk gene was amplified by PCR from the chromosome DNA of these target clones, and it was confirmed that the about 2.8 kb fragment including $Km^r$ gene, not the original fragment of about 1.5 kb, was amplified. It was also confirmed that the inosine-guanosine kinase activity was not detected in them. The inosine-guanosine kinase activity was measured according to the method of Usuda et al. (Biochim. Biophys. Acta., 1341, 200-206 (1997)). Those clones were considered strains deficient in gsk, and clones derived from the strain FDR-18 (purF$^-$, deoD$^-$, purR$^-$) and the strain FADRadd-8-3 (purF$^-$, purA$^-$, deoD$^-$, purR$^-$, add$^-$) are designated as strain FDRG-18-13 and strain FADRaddG-8-3, respectively.

2) Evaluation of Purine Nucleoside-Producing Ability of Desensitized Type purF Plasmid-Introduced Strain Because the plasmids pKFpurFKQ and pKFpurFKQPW have the $Km^r$ gene as a drug selection marker and the host strains FDRG-18-13 (purF$^-$, deoD$^-$, purR$^-$, gsk$^-$) and FADRaddG-8-3 (purF$^-$, purA$^-$, deoD$^-$, purR$^-$, add$^-$, gsk$^-$) prepared in Section 1) are made kanamycin resistant, it is difficult to obtain transformants by introducing pKFpurFKQ and pKFpurFKQPW into the strains FDRG-18-13 and FADRaddG-8-3 for the evaluation of the purine nucleoside-producing ability. Therefore, exchange of drug selection marker genes of the plasmids pKFpurFKQ and pKFpurFKQPW was performed by using pUC18 vector having the ampicillin resistance gene (Takara Shuzo). Because the locational relationship between the lac promoter and the multi-cloning site is common to pKF18 and pUC18, purFKQ and purFKQPW fragments were excised from pKFpurFKQ and pKFpurFKQPW by using PstI and HindIII, and these were inserted between the PstI and HindIII sites of pUC18 to prepare pUCpurFKQ and pUCpurFKQPW. The hosts, the strains FDRG-18-13 and FADRaddG-8-3, were transformed with the pUCpurFKQ and pUCpurFKQPW, and the purine nucleoside-producing abilities of the recombinants were evaluated. The basal medium and the culture method for the purine nucleoside production and the analysis method were the same as Example 1. For the strains of purA$^-$ (adenine auxotrophic), 5 mg/L of adenine was added to the MS medium.

The results of the evaluation of the purine nucleoside-producing ability are shown in Table 5. From these results, it was revealed that the microorganisms accumulated guanosine as well as inosine when the deficiency of gsk was added.

TABLE 5

Evaluation of purine nucleoside-producing ability

| | | Purine nucleoside accumulation | |
|---|---|---|---|
| Host | Plasmid | Inosine (mg/L) | Guanosine (mg/L) |
| W3110 | — | Trace | 0 |
| FDRG-18-13 | pUCpurFKQ | 105 | 139 |
| FDRG-18-13 | pUCpurFKQPW | 108 | 93 |
| FADRaddG-8-3 | pUCpurFKQ | 126 | 52 |
| FADRaddG-8-3 | pUCpurFKQPW | 222 | 49 |

3) Breeding of Strains Having Desensitized Type purF Integrated into Chromosome and Evaluation of Purine Nucleoside-Producing Ability The strains FDRG-18-3 (purF$^-$, deoD$^-$, purR$^-$, gsk$^-$) and FADRaddG-8-3 (purF$^-$, purA$^-$, deoD$^-$, purR$^-$, add$^-$, gsk$^-$) were transformed at 30° C. with the plasmids pMAN997purFLKQ and pMAN997purFLKQPW, respectively. Some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. From ampicillin-sensitive clones, clones grown on the minimal medium were further selected for the strain FDRG-18-13 (purF$^-$, deoD$^-$, purR$^-$, gsk$^-$), and clones grown in the minimal medium supplemented with 100 mg/L of L-histidine and 50 mg/L of adenine were selected for the strain FADRaddG-8-3 (purF$^-$, purA$^-$, deoD$^-$, purR$^-$, add$^-$, gsk$^-$).

Chromosome DNAs of these target clones were prepared, and fragments of about 1.5 kb including purF were amplified by PCR, and sequenced around the locations where the mutations were introduced thorough substitution by homologous recombination. As a result, it was confirmed that they had a mutation of K326Q (326Lys→Gln) and K326Q (326Lys→Gln)+P410W (410Pro→Trp), respectively.

The strains derived from the strain FDRG-18-13 (purF$^-$, deoD$^-$, purR$^-$, gsk$^-$) were designated as strain FDRG-18-13::KQ (purFKQ, deoD$^-$, purR$^-$, gsk$^-$) and strain FDRG-18-13::KQPW (purFKQPW, deoD$^-$, purR$^-$, gsk$^-$), and those derived from the strain FADRaddG-8-3 (purF$^-$, purA$^-$, deoD$^-$, purR$^-$, add$^-$, gsk$^-$) were designated as strain FADRaddG-8-3::KQ (purFKQ, purA$^-$, deoD$^-$, purR$^-$, add$^-$, gsk$^-$) and strain FADRaddG-8-3::KQPW (purFKQPW, purA$^-$, deoD$^-$, purR$^-$, add$^-$, gsk$^-$).

The strain FADRaddG-8-3::KQ (purFKQ, purA⁻, deoD⁻, purR⁻, add⁻, gsk⁻) was given a private number AJ13334. This strain was deposited at National Institute of Bioscience and Human-Technology of Ministry of International Trade and Industry (1-3, Higashi 1-chome, Tsukuba-shi, Ibaraki 305-0046 Japan) on Jun. 24, 1997 as an international deposition under the Budapest treaty, and received an accession number FERM BP-5993.

The purine nucleoside-producing abilities of these four kinds of strains having desensitized type purF integrated into chromosome were evaluated. The basal medium and the culture method for the purine nucleoside production and the analysis method were the same as Example 1. For the strains of purA⁻ (adenine auxotrophic), 5 mg/L of adenine was added to the MS medium.

The results of the evaluation of the purine nucleoside-producing ability are shown in Table 6. From these results, it was revealed that the microorganisms accumulated guanosine as well as inosine when the deficiency of gsk was added.

TABLE 6

Evaluation of purine nucleoside-producing ability

| Strain | Purine nucleoside accumulation | |
|---|---|---|
| | Inosine (mg/L) | Guanosine (mg/L) |
| W3110 | Trace | 0 |
| FDRG-18-13::KQ | 150 | 140 |
| FDRG-18-13::KQPW | 145 | 125 |
| FADRaddG-8-3::KQ | 550 | 135 |
| FADRaddG-8-3::KQPW | 530 | 130 |

Example 5

1) Construction of Wild Type purR Plasmid for Homologous Recombination and Breeding of Strain Having Reversed purR⁺ Integrated into Chromosome In Example 1, Section 4), the plasmid (pUCpurR) carrying the purR fragment of about 1.8 kb between the SaI site and the SphI site of pUC19 vector (Takara Shuzo) was obtained. The pUCpurR was digested with SacI and SphI to prepare a fragment of about 1.8 kb that included wild type purR. This fragment was inserted between the SacI site and the SphI site of pMAN997, which is a vector for homologous recombination having a temperature-sensitive replication origin (tsori) (described above), to obtain plasmid pMAN997purR. The strain FADRadd-8-3 (purF⁻, purA⁻, deoD⁻, purR⁻, add⁻) was transformed at 30° C. with the plasmid pMAN997purR, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. 10 clones were randomly selected from the ampicillin-sensitive clones, and the purR fragments of about 1.8 kb were amplified from the chromosome DNA of these clones by PCR. Clones in which the amplified fragment was digested with PmaCI but not with BglII were selected. The clones were considered purR⁺ reversed strains, and designated as FADadd-8-3-2 (purF⁻, purA⁻, deoD⁻, add⁻).

2) Evaluation of Purine Nucleoside-Producing Ability of Desensitized Type purF-Introduced Strain A transformant was produced by introducing pKFpurFKQ into the strain FADadd-8-3-2 (purF⁻, purA⁻, deoD⁻, add⁻), and purine nucleoside-producing ability of the strain was evaluated. For the strain FADRadd-8-3, a transformant with pKFpurKQ was also prepared, and an effect of purR deficiency was evaluated by comparison. The basal medium and the culture method for the purine nucleoside production and the analysis method were the same as Example 1. The MS medium was supplemented with 5 mg/L adenine.

The results of the evaluation of the purine nucleoside-producing ability are shown in Table 7. Superior inosine production was observed in FADRadd (purR⁻ type) compared with FADadd (purR wild type) and the effect of purR deficiency was confirmed.

TABLE 7

Evaluation of purine nucleoside-producing ability

| Host | Plasmid | Purine nucleoside accumulation | |
|---|---|---|---|
| | | Inosine (mg/L) | Guanosine (mg/L) |
| W3110 | — | Trace | 0 |
| FADRadd-8-3 | pKFpurFKQ | 1080 | 0 |
| FADadd-8-3-2 | pKFpurFKQ | 930 | 0 |

Example 6

1) Rebreeding of Strain Deficient in Inosine-Guanosine Kinase Gene (gsk)

PCR was carried out (94° C., 30 sec; 55° C., 1 min; 72° C., 2 min; 30 cycles; Gene Amp PCR System Model 9600, Perkin Elmer) by using the chromosome DNA of the strain W3110 and 32-mer and 29-mer primers for both ends, having nucleotide sequences of CTCGGTACCCTGTTGCGTTAAGC-CATCCCAGA (SEQ ID NO: 16) and CTCGCATGC-CAACGTACGGCATTAACCTA (SEQ ID NO: 17), and prepared based on the information of a gene data bank (Gen-Bank Accession No. D00798), and an amplified fragment of about 3.0 kb including the gsk structural gene region (about 800 bp) covering ATG and the translation termination codon was cloned between the KpnI site and the SphI site of pUC19 vector (Takara Shuzo) A KpnI site and a SphI site are respectively provided in the PCR primers.

Figure 3:
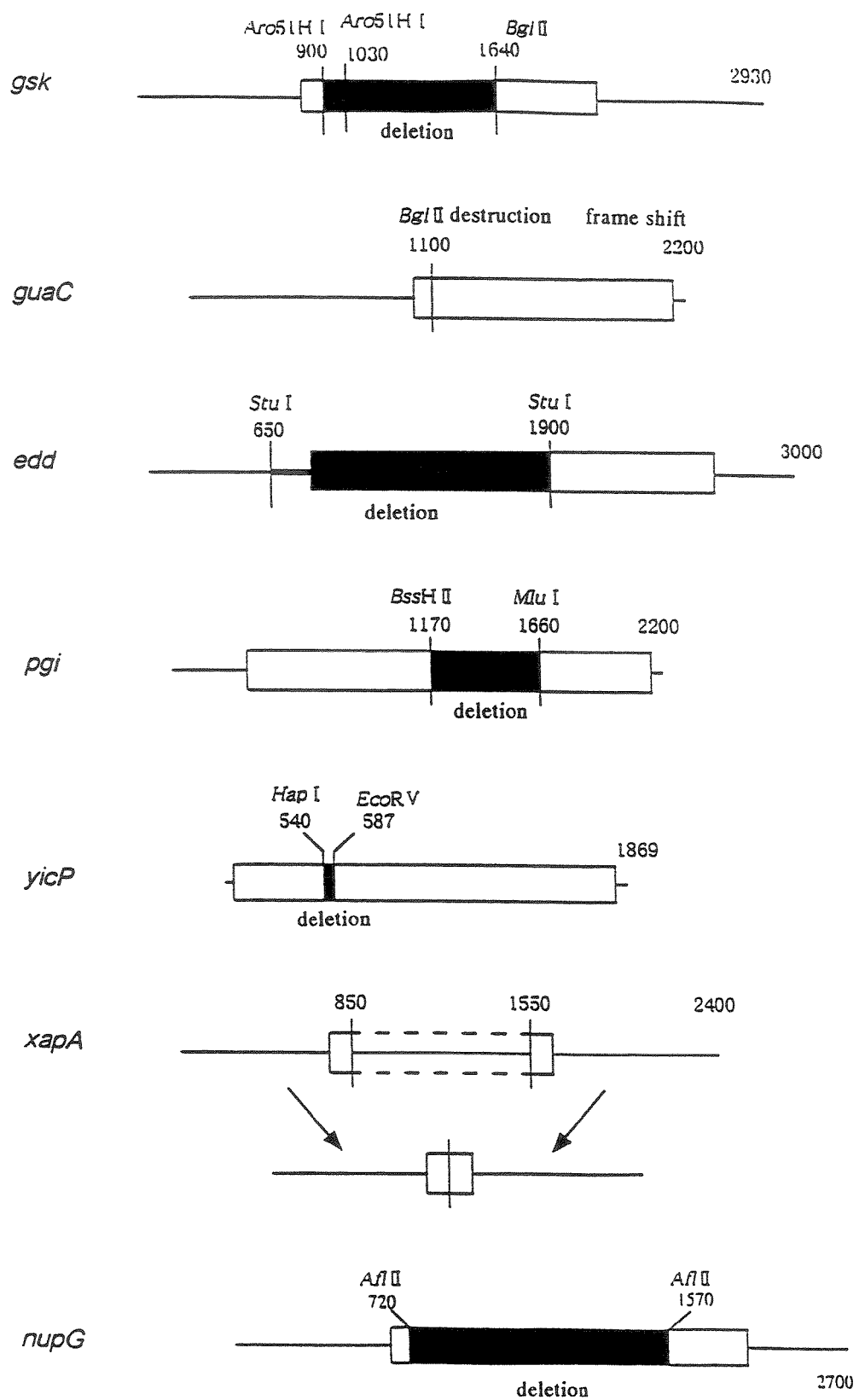
FIG. 3 shows structures of genes for homologous recombination. Numerals in the figure represent lengths (bp) of obtained fragments and positions from 5' ends.

The cloned gsk fragment of 3.0 kb contained two Aro51HI sites at about 900 bp and 1030 bp and one BglII site at about 1640 bp from the 5 end, and therefore the plasmid was digested with Aro51HI and BglII, and blunt-ended by T4 DNA polymerase. Then the Aro51HI-BglII fragment was removed and DNA of the vector was subjected to self-ligation by T4 DNA ligase. Competent cells of *E. coli* JM109 were transformed with this ligation solution, and transformants grown on LB agar plates containing 25 μg/ml of ampicillin were obtained. Plasmid DNAs were prepared from the transformants of 10 clones, and a plasmid DNA which was not digested with Aro51HI or BglII and from which plasmid a fragment of about 2.3 kp was excised by KpnI and SphI digestion (pUC19gsk'#10) was selected from the plasmid DNAs. The gsk contained in this plasmid has a deletion in the structural gene between the Aro51HI site and the BglII site, and therefore it is predicted that the encoded enzyme lacks its function (FIG. 3).

Then, the pUC19gsk #10 was digested with KpnI and SphI to prepare a fragment of about 2.3 kb that included the gsk gene. The fragment was inserted between the KpnI and SphI sites of pMAN997, which is a vector for homologous recombination having a temperature-sensitive replication origin (tsori) (describe above), to obtain plasmid pMAN997gsk#10. The strain FADRadd-8-3 (purF$^-$, purA$^-$, deoD$^-$, purR$^-$, add$^-$) was transformed at 30° C. with the plasmid pMAN997gsk'#10, and some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. Furthermore, 10 clones were randomly selected from the ampicillin-sensitive clones, the fragments including the gsk gene were amplified by PCR using the above PCR primers from the chromosome DNA of these target clones, and the clones in which the fragment of about 2.3 kb, not the original fragment of about 3.0 kb were amplified were selected. It was also confirmed that the inosine-guanosine kinase activity was not detected in them. The inosine-guanosine kinase activity was measured according to the method of Usuda et al. (Biochim. Biophys. Acta., 1341, 200-206 (1997)). The clones were considered new strains deficient in gsk, and the clones derived from the strain FADRadd-8-3 (purF$^-$, purA$^-$, deoD$^-$, purR$^-$, add$^-$) were designated as FADRaddgsk (purF$^-$, purA$^-$, deoD$^-$, purR$^-$, add$^-$, gsk$^-$).

2) Breeding of Strain Deficient in GMP Reductase Gene (guaC)

PCR was carried out (94° C., 30 sec; 55° C., 1 min; 72° C., 2 min; 30 cycles; Gene Amp PCR System Model 9600, Perkin Elmer) by using the chromosome DNA of the strain W3110 and 29-mer primers for both ends, having nucleotide sequences of CTCAAGCTTACGGCTCTGGTCCACGC-CAG (SEQ ID NO: 18) and CTCCTGCAGCAGCGTTGG-GAGATTACAGG (SEQ ID NO: 19), and prepared based on the information of a gene data bank (*E. coli* Gene Bank), and an amplified fragment of about 2.2 kb including the guaC structural gene region covering SD-ATG and the translation termination codon was cloned between the HindIII site and the PstI site of pUC18 vector (Takara Shuzo). A HindIII site and a PstI site are respectively provided in the PCR primers.

The cloned guaC fragment of 2.2 kb contained one BglII site at about 1.1 kb from the 5' end, and therefore the plasmid was digested with BglII, blunt-ended by T4 DNA polymerase and ligated with T4 DNA ligase. Competent cells of *E. coli* JM109 were transformed with this ligation solution, and transformants grown on LB agar plates containing 25 μg/ml of ampicillin were obtained. Plasmid DNAs were prepared from the transformants of 18 clones, and a plasmid DNA from which a fragment of about 2.2 kp was excised by HindIII and PstI digestion, and which fragment was not digested with BglII (pUC18guaC'#1) was selected from the plasmid DNAs. The guaC contained in this plasmid has a frame shift at the BglII site, and therefore it is predicted that the encoded enzyme lacks its function (FIG. 3).

Then, the pUC18guaC'#1 was digested with HindIII and PstI to prepare a fragment of about 2.2 kb that included guaC. The fragment was inserted between the HindIII and PstI sites of pMAN997, which is a vector for homologous recombination having a temperature-sensitive replication origin (tsori) (describe above), to obtain plasmid pMAN997guaC'#1. The strain FADRadd-8-3 (purF$^-$, purA$^-$, deoD$^-$, purR$^-$, add$^-$) and the strain FADRaddgsk (purF$^-$, purA$^-$, deoD$^-$, purR$^-$, add$^-$, gsk$^-$) were transformed at 30° C. with the plasmid pMAN997guaC'#1, and some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. The fragments of about 2.2 kb including guaC were amplified by PCR from the chromosome DNA of these target clones, and it was confirmed that the fragment was not digested with BglII. The clones satisfying the above conditions were considered strains deficient in guaC, and the clones derived from the strains FADRadd-8-3 and FADRaddgsk are designated as FADRaddguaC (purF$^-$, purA$^-$, deoD$^-$, purR$^-$, add$^-$, guaC$^-$) and FADRaddgskguaC (purF$^-$, purA$^-$, deoD$^-$, purR$^-$, add$^-$, gsk$^-$, guaC$^-$), respectively. It was also confirmed that the GMP reductase activity was not detected in them. The GMP reductase activity was measured according to the method of B. B. Garber et al. (J. Bacteriol., 43, 105 (1980)).

3) Evaluation of Purine Nucleoside-Producing Ability of Desensitized Type purF Plasmid-Introduced Strain Transformants were produced by introducing pKFpurFKQ into the strain FADRaddguaC (purF$^-$, purA$^-$, deoD$^-$, purR$^-$, add$^-$, guaC$^-$) and FADRaddgskguaC (purF$^-$, purA$^-$, deoD$^-$, purR$^-$, add$^-$, gsk$^-$, guaC$^-$) produced in Section 2), and purine nucleoside-producing abilities of the strains were evaluated. The basal medium and the culture method for the purine nucleoside production and the analysis method were the same as Example 1. The MS medium was supplemented with 5 mg/L adenine.

The results of the evaluation of the purine nucleoside-producing ability are shown in Table 8. A certain level of improvement in guanosine production was observed by the deficiency of guaC.

TABLE 8

Evaluation of purine nucleoside-producing ability

| Host | Plasmid | Purine nucleoside accumulation | |
|---|---|---|---|
| | | Inosine (mg/L) | Guanosine (mg/L) |
| FADRadd-8-3 | pKFpurFKQ | 1080 | 0 |
| FADRaddguaC | pKFpurFKQ | 670 | 20 |
| FADRaddgsk | pKFpurFKQ | 920 | 140 |
| FADRaddgskguaC | pKFpurFKQ | 750 | 180 |

Example 7

1) Breeding of Strain Deficient in 6-phosphogluconate Dehydrase Gene (edd)

PCR was carried out (94° C., 30 sec; 55° C., 1 min; 72° C., 2 min; 30 cycles; GeneAmp PCR System Model 9600, Perkin Elmer) by using the chromosome DNA of the strain W3110 and 29-mer primers for both ends, having nucleotide sequences of CTCGAATTCGGATATCTGGAAGAA-GAGGG (SEQ ID NO: 20) and CTCAAGCTTGGAAT-AGTCCCTTCGGTAGC (SEQ ID NO: 21), and prepared based on the information obtained through searching of a gene data bank (*E. coli* Gene Bank) using "edd" as a key word, and an amplified fragment of about 3.0 kb including the edd structural gene region covering ATG and the translation termination codon, about 810 bp 5' upstream region of ATG and about 360 bp downstream region of the translation termination codon was cloned into pCRTMII vector (Invitrogen) as it was. The amplified fragment of the PCR product can be cloned into this vector as it is. The vector has EcoRI sites as restriction sites at vicinities of the both sides of the cloning site. A BamHI site and a HindIII site are respectively provided in the PCR primers. The cloned edd fragment of 3.0 kb contained two StuI sites at about 660 bp and 1900 bp from the 5' end, and therefore the plasmid was digested with StuI. Then the StuI fragment of about 1.25 kb was removed and DNA of the vector was subjected to self-ligation by T4 DNA ligase. Competent cells of *E. coli* HB101 were transformed with this ligation solution, and transformants grown on LB agar plates containing 25 μg/ml of ampicillin were obtained. Plasmid DNAs were prepared from the transformants of 10 clones, and a plasmid DNA from which a fragment of about 1.25 kp was not excised by StuI (pCRTMIIedd'#1) was selected from the plasmid DNAs. The edd contained in this plasmid has a deletion of a protein-coding region including a promoter region, and therefore it is predicted that the enzyme is not formed (FIG. 3).

Then, the pCRTMIIedd'#1 was digested with EcoRI to prepare a fragment of about 1.75 kb that included a part of edd and a flanking region thereof. The fragment was inserted into the EcoRI site of pMAN997, which is a vector for homologous recombination having a temperature-sensitive replication origin (tsori) (describe above), to obtain plasmid pMAN997edd'#1. The strain FADRadd-8-3 (purF$^-$, purA$^-$, deoD$^-$, purR$^-$, add$^-$) was transformed at 30° C. with the plasmid pMAN997edd'#1, and some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. The edd regions were amplified by PCR using the above PCR primers from the chromosome DNA of these target clones, and the clones in which the size of the amplified fragment is about 1.75 kb of deletion type, not about 3.0 kb of wild type were selected. The clones were considered strains deficient in edd and designated as FADRaddedd (purF$^-$, purA$^-$, deoD$^-$, purR$^-$, add$^-$, edd$^-$).

2) Evaluation of Purine Nucleoside-Producing Ability of Desensitized Type purF Plasmid-Introduced Strain A transformant was produced by introducing pKFpurFKQ into the strain FADRaddedd (purF$^-$, purA$^-$, deoD$^-$, purR$^-$, add$^-$, edd$^-$) bred in Section 1), and purine nucleoside-producing ability of the strain was evaluated. The basal medium and the culture method for the purine nucleoside production and the analysis method were the same as Example 1. The MS medium was supplemented with 5 mg/L adenine. The 6-phosphogulconate dehydrase encoded by edd is an enzyme which is induced by gluconic acid and positioned at the first step in the Entner-Doudoroff pathway metabolizing gluconate to pyruvate. Because the gluconate was considered to flow only into the pentose phosphate pathway by deficiency of this enzyme, gluconic acid (48 g/L added) was used as a carbon source other than glucose to carry out the evaluation.

The results of the evaluation of the purine nucleoside-producing ability are shown in Table 9. Remarkable improvement in inosine production was observed by the deficiency of edd, when the gluconic acid was used as the carbon source. The effect was also observed when glucose was used as the carbon source.

TABLE 9

Evaluation of purine nucleoside-producing ability

| Host | Plasmid | Carbon source | Purine nucleoside accumulation | |
|---|---|---|---|---|
| | | | Inosine (mg/L) | Guanosine (mg/L) |
| FADRadd-8-3 | pKFpurFKQ | Glucose | 1080 | 0 |
| FADRaddedd | pKFpurFKQ | Glucose | 1340 | 0 |
| FADRadd-8-3 | pKFpurFKQ | Gluconic acid | 1050 | 0 |
| FADRaddedd | pKFpurFKQ | Gluconic acid | 2600 | 0 |

Example 8

1) Breeding of Strain Deficient in Phosphoglucose Isomerase Gene (pgi)

PCR was carried out (94° C., 30 sec; 55° C., 1 min; 72° C., 2 min; 30 cycles; Gene Amp PCR System Model 9600, Perkin Elmer) by using the chromosome DNA of the strain W3110 and 29-mer primers for both ends, having nucleotide sequences of CTCGTCGACTCCATTTTCAGCCTTG-GCAC (SEQ ID NO: 22) and CTCGCATGCGTCGCAT-CAGGCATCGGTTG (SEQ ID NO: 23), and prepared based on the information obtained through searching of a gene data bank (*E. coli* Gene Bank) using "pgi" as a key word, and an amplified fragment of about 2.2 kb including the pgi structural gene region covering ATG and the translation termination codon was cloned between the SalI site and the SphI site of pUC18 vector (Takara Shuzo). A SalI site and a SphI site are respectively provided in the PCR primers. The cloned pgi fragment of 2.2 kb contained one BssHII site and one MluI site at about 1170 bp and 1660 bp from the 51 end, respectively, and therefore the plasmid was digested with BssHII and MluI, and blunt-ended by T4 DNA polymerase. Then the fragment of about 500 bp between the BssHII site and the MluI site was removed and DNA of the vector was subjected to self-ligation by T4 DNA ligase. Competent cells of *E. coli* JM109 were transformed with this ligation solution, and transformants grown on LB agar plates containing 25 μg/ml of ampicillin were obtained. Plasmid DNAs were prepared from the transformants of 10 clones, and a plasmid DNA from which a fragment of about 1.7 kp was excised by SalI and SphI digestion (pUC18 pgi'#1) was selected from the plasmid DNAs. The pgi contained in this plasmid has a deletion between the BssHII site and the MluI site, and therefore it is predicted that the encoded enzyme lacks its function (FIG. 3).

Then, the pUC18 pgi'#1 was digested with SalI and SphI to prepare a fragment of about 1.7 kb that included pgi. The fragment was inserted between the SalI site and the SphI site of pMAN997, which is a vector for homologous recombination having a temperature-sensitive replication origin (tsori) (describe above), to obtain plasmid pMAN997 pgi'#1. The strain FADRadd-8-3 (purF−, purA−, deoD−, purR−, add−) and the strain FADRaddedd (purF−, purA−, deoD−, purR−, adds, edd−) were transformed at 30° C. with the plasmid pMAN997 pgi'#1, and some of the obtained colonies were each streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. The pgi regions were amplified by PCR using the above PCR primers from the chromosome DNA of these target clones, and the clones in which the size of the amplified fragment was about 1.7 kb of deletion type, not about 2.2 kb of wild type were selected. The clones were considered strains deficient in pgi, and clones derived from FADRadd-8-3 and FADRaddedd were designated as FADRaddpgi (purF−, purA−, deoD−, purR−, add−, pgi−) and FADRaddeddpgi (purF−, purA−, deoD−, purr, add−, edd, pgi−), respectively.

2) Evaluation of Purine Nucleoside-Producing Ability of Desensitized Type purF Plasmid-Introduced Strain Transformants were produced by introducing pKFpurFKQ into the strain FADRaddpgi (purF−, purA−, deoD−, purR−, add−, pgi−) and the strain FADRaddeddpgi (purF−, purA−, deoD−, purR−, add−, edd−, pgi−) bred in Section 1), and purine nucleoside-producing abilities of the strains were evaluated. The basal medium and the culture method for the purine nucleoside production and the analysis method were the same as Example 1 provided that the amount of yeast extract in the MS medium (basal medium) which was a medium used for evaluation of production was increased to 0.8%.

The results of the evaluation of the purine nucleoside-producing ability are shown in Table 10. By deficiency of pgi, growth remarkably lowered in the MS medium supplemented with 5 mg/L of adenine which was used in the above Examples. Therefore, the medium in which the amount of yeast extract was increased to 0.8% was used. In this medium, the pgi+ parent strain showed increase of the growth rate, lowering of inosine production and by-production of hypoxanthine. On the contrary, remarkable improvement in inosine production was observed in the strain deficient in pgi.

TABLE 10

Evaluation of purine nucleoside-producing ability

| Host | Plasmid | Purine nucleoside accumulation | |
|---|---|---|---|
| | | Inosine (mg/L) | Hypoxanthine (mg/L) |
| FADRadd-8-3 | pKFpurFKQ | 450 | 260 |
| FADRaddpgi | pKFpurFKQ | 2770 | 100 |
| FADRaddedd | pKFpurFKQ | 780 | 210 |
| FADRaddeddpgi | pKFpurFKQ | 3080 | 120 |

Example 9

1) Breeding of Strain Deficient in Adenine Deaminase Gene (yicP)

In a gene data bank (*E. coli* Gene Bank), yicP is registered as ORF (open reading frame, structural gene) which has a high homology with adenine deaminase from *Bacillus subti-*

*lis.* PCR was carried out (94° C., 30 sec; 55° C., 1 min; 72° C., 2 min; 30 cycles; Gene Amp PCR System Model 9600, Perkin Elmer) by using the chromosome DNA of the strain W3110 and 29-mer primers for both ends, having nucleotide sequences of CTCCTGCAGCGACGTTTTCTTTTAT-GACA (SEQ ID NO: 24) and CTCAAGCTTCGTAACTG-GTGACTTTTGCC (SEQ ID NO: 25), and prepared based on the information obtained through searching using "yicP" as a key word, to amplify a fragment of about 1.9 kb including the yicP structural gene region covering ATG and the translation termination codon, about 50 bp 5' upstream region of ATG and about 40 bp downstream region of the translation termination codon. A PstI site and a HindIII site are respectively provided in the PCR primers. The PCR product was digested with PstI and HindIII, and cloned between the PstI site and the HindIII site of pUC18 vector (Takara Shuzo). The cloned yicP fragment of 1.9 kb contained one HapI site and one EcoRV site at about 540 bp and 590 bp from the 5' end, respectively, and therefore the plasmid was digested with HapI and EcoRV. Then the HapI-EcoRV fragment of 47 bp was removed and DNA of the vector was subjected to self-ligation by T4 DNA ligase. Competent cells of *E. coli* JM109 were transformed with this ligation solution, and transformants grown on LB agar plates containing 25 μg/ml of ampicillin were obtained. Plasmid DNAs were prepared from the transformants of 10 clones, and a plasmid DNA which was not digested with HapI or EcoRV (pUC18yicP'#1) was selected from the plasmid DNAs. The yicP contained in this plasmid has a frame shift due to a deletion of 47 bp of HapI-EcoRV sites, and therefore it is predicted that the encoded enzyme lacks its function (FIG. 3).

Then, the pUC18yicP'#1 was digested with PstI and HindIII to prepare a fragment of about 1.9 kb that included the yicP gene. The fragment was inserted between the PstI site and the HindIII site of pMAN997, which is a vector for homologous recombination having a temperature-sensitive replication origin (tsori) (describe above), to obtain plasmid pMAN997yicP'#1. The strain FADRaddedd (purF−, purA−, deoD−, purR−, add−, edd−) was transformed at 30° C. with the plasmid pMAN997yicP'#1, and some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. The yicP regions were amplified by PCR using the above PCR primers from the chromosome DNA of these target clones, and the clones in which the size of the amplified fragment was not digested with HapI or EcoRV were selected. It was also confirmed that the adenine deaminase activity was not detected in these clones. The adenine deaminase activity was measured according to the method of Per Nygaard et al. (J. Bacteriol., 178, 846-853 (1996)). The clones were considered strains deficient in yicP, and designated as FADRaddeddyicP (purF−, purA−, deoD−, purR−, add−, eddy, yicP−).

2) Breeding of Strain Deficient in Phosphoglucose Isomerase Gene (pgi) from Strain Deficient in Adenine Deaminase Gene (yicP)

The deficiency of pgi was also added to the strain FADRaddeddyicP (purF−, purA−, deoD−, purR−, add−, eddy, yicP−). By using pMAN997 pgi'#1 constructed in Example 8, a strain FADRaddeddyicPpgi (purF−, purA−, deoD−, purR−, add−, edd−, yicP−, pgi−) was obtained in the same method as in Example 8.

3) Evaluation of Purine Nucleoside-Producing Ability of Desensitized Type purF Plasmid-Introduced Strain Transformants were produced by introducing pKFpurFKQ into the strain FADRaddeddyicP (purF−, purA−, deoD−, purR−, add−, edd−, yicP−) and the strain FADRaddeddyicPpgi (purF−, purA−, deoD−, purR−, add−, eddy, yicP−, pgi−) bred in Sections 1) and 2), and responses of growth to an adenine amount and purine nucleoside-producing abilities of the strains were evaluated. The basal medium and the culture method for the purine nucleoside production and the analysis method were the same as Example 1 provided that the used medium was the MS medium to which adenine was added in an amount between 0 to 50 mg/L.

The results of the evaluation of the growth response to adenine and the purine nucleoside-producing ability are shown in Table 11. By deficiency of yicP, the growth rate with respect to adenine was improved and an effect of the deficiency of yicP was observed when adenine was added in amounts of 50 mg/L and 20 mg/L.

TABLE 11

Evaluation of purine nucleoside-producing ability

| Host | Plasmid | Adenine added (mg/L) | Growth rate (OD) | Purine nucleoside accumulation | |
|---|---|---|---|---|---|
| | | | | Inosine (mg/L) | Hypoxanthine (mg/L) |
| FADRaddedd | pKFpurFKQ | 0 | 2.2 | 870 | 0 |
| | | 50 | 3.2 | 650 | 0 |
| FADRaddeddyicP | pKFpurFKQ | 0 | 2.4 | 870 | 0 |
| | | 50 | 6.8 | 1100 | 40 |
| FADRaddeddpgi | pKFpurFKQ | 5 | 2.2 | 1420 | 28 |
| | | 20 | 3.4 | 1760 | 48 |

TABLE 11-continued

Evaluation of purine nucleoside-producing ability

| Host | Plasmid | Adenine added (mg/L) | Growth rate (OD) | Purine nucleoside accumulation | |
|---|---|---|---|---|---|
| | | | | Inosine (mg/L) | Hypoxanthine (mg/L) |
| FADRaddeddyicPpgi | pKFpurFKQ | 5 | 2.1 | 1380 | 7 |
| | | 20 | 3.7 | 2350 | 19 |

Example 10

1) Preparation of PRPP Synthetase Gene (prs)

PCR was carried out (94° C., 30 sec; 55° C., 1 min; 72° C., 2 min; 30 cycles; GeneAmp PCR System Model 9600, Perkin Elmer) by using the chromosome DNA of the strain W3110 and 38-mer and 29-mer primers for both ends, having nucleotide sequences of CTCGTCGACTGCCTAAGGATCT-TCTCATGCCTGATATG (SEQ ID NO: 26) and CTCGCAT-GCGCCGGGTTCGATTAGTGTTC (SEQ ID NO: 27), and prepared based on the information of a gene data bank (*E. coli* Gene Bank), and an amplified fragment of about 1 kb including the prs structural gene region covering SD-ATG and the translation termination codon was cloned into pUC18 vector (Takara Shuzo). A SalI site and a SphI site are respectively provided in the PCR primers. The PCR product was digested with SalI and SphI, and cloned between the SalI site and the SphI site of pUC18 vector (pUCprs).

2) Construction of Desensitized Type prs

A prs fragment was excised from the plasmid carrying the prs of about 1 kb cloned in Section 1) by SalI and SphI digestion, and inserted between the SalI and SphI sites of the multi-cloning site of a plasmid for introducing mutation, pKF19k (Takara Shuzo) to obtain the target clone (pKFprs). S. G. Bower et al. (J. Biol. Chem., 264, 10287 (1989)) has suggested that PRPP synthetase (Prs) is subjected to feedback inhibition by AMP and ADP. It is also described that the enzyme whose Asp (D) at position 128 is mutated to Ala (A) is partially desensitized. Therefore, the following synthetic DNA primer was prepared for gene substitution realizing mutation of Asp (D) at position 128 PRPP synthetase (Prs) to Ala (A), and pKFprs was subjected to site-directed mutagenesis according to the protocol of Site-directed Mutagenesis System Mutan-Super Express Km (Takara Shuzo) to introduce a site-directed mutation into the pKFprs.

Primer for D128A mutation:
(SEQ ID NO:28)
5'-GCGTGCAGAGCCACTATCAGC-3'

After the mutagenesis, 12 clones were randomly picked up from the resulting transformants, and plasmids were produced from them. By nucleotide sequencing of the plasmids around the locations where the mutations were introduced, it was confirmed that 9 clones of target mutants were obtained. The prs fragment was excised with SalI and SphI from pKF-prsDA having the mutant type prs, and inserted between the SalI site and the SphI site of pUC18 and pSTV18 (Takara Shuzo). For using the wild type prs as a control, the prs fragment was excised with SalI and SphI from pUCprs constructed in the above, and inserted between the SalI site and the SphI site of pSTV18 (Takara Shuzo). Each of the plasmids pUCprsDA and pSTVprsDA and the plasmids pUCprs and pSTVprs has an inserted mutant prs or wild type prs downstream of the lacp/o (promoter of lactose operon) derived from pUC18 and pSTV18, respectively, and the prs is expressed under the control of this promoter.

Recombinant bacteria obtained by transforming *E. coli* JM109 cells with the above four plasmids were cultured in LB liquid medium for eight hours, and collected, and crude enzyme extracts were prepared from them. The PRPP synthetase activity of the extracts and degrees of inhibition by ADP were measured according to the method of K. F. Jensen et al. (Analytical Biochemistry, 98, 254-263 (1979)) which was partially modified. Specifically, [α-$^{32}$P]ATP was used as the substrate and [$^{32}$P]AMP produced by the reaction was measured. The results are shown in Table 12.

TABLE 12

PRPP synthetase (Prs) activity

| Host | Plasmid | Property | Specific activity (nmole/min/mg crude enzyme extract) | |
|---|---|---|---|---|
| | | | None | 5 mM ADP |
| JM109 | pUC18 | Control | 2.9 | ND |
| JM109 | pUCprs | High copy, wild type | 75.9 | ND |
| JM109 | pUCprsDA | High copy, mutant type | 80.8 | 20.2 |
| JM109 | pSTVprs | Medium copy, wild type | 11.5 | ND |
| JM109 | pSTVprsDA | Medium copy, mutant type | 10.6 | 2.7 |

3) Evaluation of Purine Nucleoside-Producing Ability of Desensitized Type prs Plasmid-Introduced Strain Strains each having two plasmids simultaneously were made by introducing pKFpurFKQ into the strain FADRad-deddyicPpgi (purF$^-$, purA$^-$, deoD$^-$, purR$^-$, add$^-$, edd$^-$, yicP$^-$, pgi$^-$) bred in Example 9, Section 3) to obtain a transformant and further each introducing pSTVprs and pSTVprsDA carrying prs and prsDA genes into the transformant, and purine nucleoside-producing abilities of the strains were evaluated. The basal medium and the culture method for the purine nucleoside production and the analysis method were the same as Example 1 provided that the amount of yeast extract in the MS medium was increased to 0.4%.

The results of the evaluation of the purine nucleoside-producing ability are shown in Table 13. By introduction of mutant prsDA as a plasmid, an effect of improvement in inosine production was observed.

TABLE 13

Evaluation of purine nucleoside-producing ability

| Host | Plasmid | Purine nucleoside accumulation | |
|---|---|---|---|
| | | Inosine (mg/L) | Hypoxanthine (mg/L) |
| FADRaddeddyicPpgi | pKFpurFKQ | 1600 | 8 |
| | pKFpurFKQ + pSTVprs | 1450 | 3 |
| | pKFpurFKQ + pSTVprsDA | 1815 | 10 |

Example 11

1) Breeding of Strain Deficient in Xanthosine Phosphorylase Gene (xapA)

A gene inactivated by mutation was constructed in one step by Cross-over PCR using four primers prepared based on the information obtained through searching of a gene data bank (*E. coli* Gene Bank) using "xapA" as a key word. The used primers are as follows:

```
N-out:
                                  (SEQ ID NO:29)
5'-CGCGGATCCGCGACATAGCCGTTGTCGCC-3'

N-in:
                                  (SEQ ID NO:30)
5'CCCATCCACTAAACTTAAACATCGTGGCGTGAAATCAGG-3'

C-in:
                                  (SEQ ID NO:31)
5'-TGTTTAAGTTTAGTGGATGGGCATCAACCTTATTTGTGG-3'

C-out:
                                  (SEQ ID NO:32)
5'-CGCAAGCTTCAAACTCCGGGTTACGGGCG-3'
```

First, PCR was carried out (94° C., 30 sec; 55° C., 1 min; 72° C., 2 min; 30 cycles; Gene Amp PCR System Model 9600, Perkin Elmer) by using the chromosome DNA of the strain W3110 and primers N-out (29-mer) and N-in (39-mer) as well as primers C-in (39-mer) and C-out (29-mer) for both ends, to obtain two PCR products (both are fragments of about 850 bp), respectively. Then, PCR was again carried out by using a mixture of the two PCR products as a template and the primers N-out and C-out for both ends, to amplify a gene fragment in which the gene region including the xapA structural gene region was shortened from a fragment of about 2.4 kb (size of wild type) to a fragment of about 1.7 kb. A BamHI site and a HindIII site are provided in the PCR primers N-out and C-out, respectively. This PCR product was digested with BamHI and HindIII, and the obtained fragment was ligated by T4 DNA ligase with a plasmid obtained by digesting pMAN997, which is a vector for homologous recombination having a temperature-sensitive replication origin (tsori) (describe above), with BamHI and HindIII. Competent cells of *E. coli* JM109 were transformed with this ligation solution, and transformants grown on LB agar plates containing 25 μg/ml of ampicillin were obtained. Plasmid DNAs were prepared from the transformants of 10 clones, and a plasmid DNA from which a fragment of about 1.7 kp was excised by BamHI and HindIII digestion (pMAN997xapA'#1) was selected from the plasmid DNAs. The xapA contained in this plasmid has a deletion of about 700 bp in the structural gene, and therefore it is predicted that the encoded enzyme lacks its function (FIG. 3).

The strain FADRaddeddyicPpgi (purF$^-$, purA$^-$, deoD$^-$, purR$^-$, add$^-$, eddy, yicP$^-$, pgi$^-$) was transformed at 30° C. with the plasmid pMAN997xapA'#1, and some of the obtained colonies were streaked on LB agar plates containing 25 μg/ml of ampicillin, and cultured at 30° C. overnight. Then, the cultured bacterial cells were plated on LB agar plates containing 25 μg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 μg/ml of ampicillin, respectively, and ampicillin-sensitive clones grown only on the LB agar plates were selected. The xapA region were amplified by PCR using the above PCR primers N-out and C-out from the chromosome DNA of these target clones, and the clones in which the size of the amplified fragment was about 1.7 kb were selected. The clones were considered strains deficient in xapA, and designated as FADRaddeddyicPpgixapA (purF$^-$, purA$^-$, deoD$^-$, purR$^-$, add$^-$, edd$^-$, yicP$^-$, pgi$^-$, xapA$^-$). In the strain deficient in xapA, xanthine production in a medium was not observed by culture with xanthosine supplemented, and it was confirmed that xanthosine phosphorylase was not induced. The xanthosine phosphorylase activity was measured according to the method of K. Hammer Jespersen et al. (Molec. Gen. Genet., 179, 341-348 (1980)).

2) Evaluation of Purine Nucleoside-Producing Ability of Desensitized Type purF Plasmid-Introduced Strain A transformant was produced by introducing pKFpurFKQ into the strain FADRaddeddyicPpgixapA (purF$^-$, purA$^-$, deoD$^-$, purR$^-$, add$^-$, edd$^-$, yicP$^-$, pgi$^-$, xapA$^-$) bred in Section 1), and purine nucleoside-producing ability of the strain was evaluated. The basal medium and the culture method for the purine nucleoside production and the analysis method were the same as Example 1 provided that the MS medium in which the amount of yeast extract was increased to 0.8% was used.

The results of the evaluation of the purine nucleoside-producing ability are shown in Table 14. When the amount of yeast extract in the MS medium was increased, by-production of hypoxanthine which remarkably occurred after sugar consumption in the latter half of the culture was reduced by deficiency of xapA, and improvement of inosine production was observed.

TABLE 14

Evaluation of purine nucleoside-producing ability

| Host | Plasmid | Culture period (days) | Inosine (mg/L) | Hypoxan- thine (mg/L) |
|---|---|---|---|---|
| FADRaddeddyicPpgi | pKFpurFKQ | 3 | 4640 | 146 |
|  |  | 6 | 1850 | 1500 |
| FADRaddeddyicPpgixapA | pKFpurFKQ | 3 | 5870 | 57 |
|  |  | 6 | 3810 | 915 |

Example 12

1) Breeding of Strain Deficient in Nucleoside Permease Gene (nupG)

PCR was carried out (94° C., 30 sec; 55° C., 1 min; 72° C., 2 min; 30 cycles; GeneAmp PCR System Model 9600, Perkin Elmer) by using the chromosome DNA of the strain W3110 as a template and 35-mer primers for both ends, having nucleotide sequences of CTCGAATTCATGGTGCCGAACCAC-CTTGATAAACG (SEQ ID NO: 33) and CTCGTCGACAT-GCCGAAACCGGCGAATATAGCGAC (SEQ ID NO: 34), and prepared based on the information of a gene data bank (*E. coli* Gene Bank), to amplify a fragment of about 2.7 kb of an nupG structural gene region covering SD-ATG and the translation termination codon. An EcoRI site and a SalI site are respectively provided in the PCR primers. The amplified fragment was digested with EcoRI, SalI and AflII. Since the PCR-amplified fragment contained two AflII sites, three fragments of about 750 bp, 820 bp and 1130 bp were formed. The two fragments of about 720 bp and 1130 bp other than the AflII fragment of about 820 bp were collected and were ligated by T4 DNA ligase with DNA obtained by digesting pUC18 vector (Takara Shuzo) with EcoRI and SalI. Competent cells of *E. coli* HB101 were transformed with this ligation solution, and plasmid DNAs were prepared from 16 of the emerged colonies, and a plasmid DNA in which a fragment digested with EcoRI and SalI was of about 1.9 kb (pUC18nupG'#1) was selected from the plasmid DNAs. The pUC18nupG'#1 was digested with EcoRI and SalI, and the resulting fragment of about 1.9 kb was ligated by T4 DNA ligase with a plasmid obtained by digesting pMAN997, which is a vector for homologous recombination having a temperature-sensitive replication origin (tsori) (described above), with EcoRI and SalI. Competent cells of *E. coli* JM109 were transformed with this ligation solution, and transformants grown on LB agar plates containing 25 µg/ml of ampicillin were obtained. Plasmid DNAs were prepared from the transformants of 10 clones, and a plasmid DNA from which a fragment of about 1.9 kp was excised by EcoRI and SalI digestion (pMAN997nupG'#1) was selected from the plasmid DNAs. The nupG contained in this plasmid DNA has a deletion of about 820 bp in the structural gene, and therefore it is predicted that the encoded enzyme lacks its function (FIG. 3).

The strain FADRaddeddyicPpgi (purF$^-$, purA$^-$, deoD$^-$, purR$^-$, add$^-$, edd$^-$, yicP$^-$, pgi$^-$) was transformed at 30° C. with the plasmid pMAN997nupG'#1, and some of the obtained colonies were streaked on LB agar plates containing 25 µg/ml of ampicillin, and cultured at 30° C. overnight. Then, the cultured bacterial cells were plated on LB agar plates containing 25 µg/ml of ampicillin so that single colonies should be obtained, to obtain colonies grown at 42° C. The procedure for obtaining single colonies grown at 42° C. was repeated once, and clones in which the whole plasmid was integrated into the chromosome through homologous recombination were selected. It was confirmed that these clones did not have the plasmid in their cytoplasm. Then, several clones among these clones were streaked on LB agar plates, cultured at 30° C. overnight, then inoculated into LB liquid medium (3 ml/test tube), and cultured at 42° C. for 3 to 4 hours with shaking. The culture was appropriately diluted so that single colonies should be obtained (about $10^{-5}$ to $10^{-6}$ dilution), plated on LB agar plates, and cultured at 42° C. overnight to obtain colonies. One hundred colonies were randomly picked up from the emerged colonies, and each allowed to grow on LB agar plates and LB agar plates containing 25 µg/ml of ampicillin, respectively, and ampicillin-sensitive clones grown only on the LB agar plates were selected. The nupG region were amplified by PCR using the above PCR primers from the chromosome DNA of these target clones, and clones in which the size of the amplified fragment was about 1.9 kb were selected. These clones were considered strains deficient in nupG, and designated as FADRaddeddyicPpginupG (purF$^-$, purA$^-$, deoD$^-$, purR$^-$, add$^-$, edd$^-$, yicP$^-$, pgi$^-$, nupG$^-$).

2) Evaluation of Purine Nucleoside-Producing Ability of Desensitized Type purF-Introduced Strain A transformant was made by introducing pKFpurFKQ into the strain FADRaddeddyicPpginupG (purF$^-$, purA$^-$, deoD$^-$, purR$^-$, add$^-$, edd$^-$, yicP$^-$, pgi$^-$, nupG$^-$) bred in Section 1), and purine nucleoside-producing ability of the strain was evaluated. The basal medium and the culture method for the purine nucleoside production and the analysis method were the same as Example 1 provided that the MS medium in which the amount of yeast extract was increased to 1.2%.

The results of the evaluation of the purine nucleoside-producing ability are shown in Table 15. When the amount of yeast extract in the MS medium was increased, by-production of hypoxanthine which remarkably occurred after sugar consumption in the latter half of the culture was reduced and improvement of inosine production was observed by deficiency of nupG.

TABLE 15

Evaluation of purine nucleoside-producing ability

| Host | Plasmid | Inosine (mg/L) | Hypoxanthine (mg/L) |
|---|---|---|---|
| FADRaddeddyicPpgi | pKFpurFKQ | 1190 | 835 |
| FADRaddeddyicPpginupG | pKFpurFKQ | 3390 | 315 |

INDUSTRIAL APPLICABILITY

According to the present invention, a purine nucleoside-producing bacterium is created by derepressing and desensitizing an enzyme which subjected to the control in purine nucleoside biosynthesis and further blocking a decomposition system and a conversion system. The created purine nucleoside-producing bacterium can be suitably used for production of a purine nucleoside by fermentation.

What is claimed is:

1. A method for producing a purine nucleoside by fermentation comprising:

culturing an *Escherichia coli* microorganism in a culture medium to produce and accumulate the purine nucleoside in the medium, and collecting the purine nucleoside, wherein said microorganism has purine nucleoside-producing ability and is modified to desensitize feedback inhibition of phosphoribosyl pyrophosphate amidotransferase, said phoribosyl pyrophosphate amidotransferase being encoded by a gene obtained by PCR amplification employing the primer pair of SEQ ID NO: 1 and SEQ ID NO: 2 and *Escherichia coli* chromosomal DNA as the template, wherein said microorganism is further modified to inactivate a purine repressor, said purine repressor being encoded by a gene obtained by PCR amplification employing the primer pair of SEQ ID NO: 7 and SEQ ID NO: 8 and *Escherichia coli* chromosomal DNA as the template, and wherein said microorganism is further modified to block reactions catalyzed by succinyl-adenosine monophosphate synthase, purine nucleoside phosphorylase, adenosine deaminase, and phosphoglucose isomerase, said succinyl-adenosine monophosphate synthase being encoded by a gene obtained by PCR amplification employing the primer pair of SEQ ID NO: 3 and SEQ ID NO: 4 and *Escherichia coli* chromosomal DNA as the template, said purine nucleoside phosphorylase being encoded by a gene obtained by PCR amplification employing the primer pair of SEQ ID NO: 5 and SEQ ID NO: 6 and *Escherichia coli* chromosomal DNA as the template, said adenosine deaminase being encoded by a gene obtained by PCR amplification employing the primer pair of SEQ ID NO: 11 and SEQ ID NO: 12 and *Escherichia coli* chromosomal DNA as the template, said phosphoglucose isomerase being encoded by a gene obtained by PCR amplification employing the primer pair of SEQ ID NO: 22 and SEQ ID NO: 23 and *Escherichia coli* chromosomal DNA as the template.

2. The method according to claim 1, wherein said microorganism is further modified to increase an activity of an enzyme involved in purine nucleoside biosynthesis in cells of the microorganism.

3. The method according to claim 1, wherein said microorganism is further modified to increase an expression amount of a gene for an enzyme involved in purine nucleoside biosynthesis.

4. The method according to claim 3, wherein the enzyme involved in the purine nucleoside biosynthesis is phosphoribosyl pyrophosphate amidotransferase or phosphoribosyl pyrophosphate synthetase.

5. The method according to claim 1, wherein said microorganism is further modified to block a reaction branching from purine nucleoside biosynthesis and leading to another metabolite.

6. The method according to claim 5, wherein the reaction branching from the purine nucleoside biosynthesis and leading to another metabolite is a reaction catalyzed by an enzyme selected from the group consisting of inosine-guanosine kinase, guanosine monophosphate reductase, 6-phosphogluconoate dehydrase, adenine deaminase, and xanthosine phosphorylase.

7. The method according to claim 1, wherein said microorganism is further modified to weaken incorporation of a purine nucleoside into cells of the microorganism.

8. The method according to claim 7, wherein the incorporation of the purine nucleoside into cells of the microorganism is weakened by blockage of a reaction involved in the incorporation of the purine nucleoside into cells of the microorganism, and the reaction involved in the incorporation of the purine nucleoside into cells of the microorganism is a reaction catalyzed by nucleoside permease.

9. The method according to claim 1, wherein said purine nucleoside is a purine nucleoside selected from the group consisting of inosine and guanosine.

* * * * *

SEQUENCE LISTING

<160> NUMBER OF SEQ ID NOS: 34

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
ctcctgcaga acgaggaaaa agacgtatg                                   29

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
ctcaagcttt catccttcgt tatgcatttc g                                31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
ctcgagctca tgggtaacaa cgtcgtcgta c                                31

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
ctcgtcgact tacgcgtcga acgggtcgcg c                                31

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
ctcgtcgacg cgggtctgga actgttcgac                                  30

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
ctcgcatgcc cgtgctttac caaagcgaat c                          31

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
ctcgtcgacg aaagtagaag cgtcatcag                             29

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
ctcgcatgct taacgacgat agtcgcgg                              28

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
gggcttcgtt cagaaccgct atgttgg                               27

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
tatggtattg atatgtggag cgccacggaa c                          31

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
ctcgtcgacg gctggatgcc ttacgcatc                             29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
ctcgcatgca gtcagcacgg tatatcgtg					29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
ctcaagcttg tctgatttat cacatcatc					29

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 14
ctcgagctca tgaaatttcc cgg					23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 15
ctcggatccg gtaccatgct g					21

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 16
ctcggtaccc tgttgcgtta agccatccca ga					32

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 17
ctcgcatgcc aacgtacggc attaaccta					29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 18
ctcaagctta cggctctggt ccacgccag					29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
ctcctgcagc agcgttggga gattacagg                                    29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
ctcgaattcg gatatctgga agaagaggg                                    29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
ctcaagcttg gaatagtccc ttcggtagc                                    29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
ctcgtcgact ccattttcag ccttggcac                                    29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
ctcgcatgcg tcgcatcagg catcggttg                                    29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 24
ctcctgcagc gacgtttttct tttatgaca                                   29

```
<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
ctcaagcttc gtaactggtg acttttgcc                                            29

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 26
ctcgtcgact gcctaaggat cttctcatgc ctgatatg                                  38

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
ctcgcatgcg ccgggttcga ttagtgttc                                            29

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
gcgtgcagag ccactatcag c                                                    21

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
cgcggatccg cgacatagcc gttgtcgcc                                            29

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 30
cccatccact aaacttaaac atcgtggcgt gaaatcagg                                 39
```

-continued

```
<210> SEQ ID NO 31
<211> LENGTH: 39
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 31
tgtttaagtt tagtggatgg gcatcaacct tatttgtgg                              39

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 32
cgcaagcttc aaactccggg ttacgggcg                                         29

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 33
ctcgaattca tggtgccgaa ccaccttgat aaacg                                  35

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 34
ctcgtcgaca tgccgaaacc ggcgaatata gcgac                                  35
```